United States Patent [19]
Bauer et al.

[11] Patent Number: 5,788,688
[45] Date of Patent: Aug. 4, 1998

[54] SURGEON'S COMMAND AND CONTROL

[75] Inventors: James D. Bauer, Frankfort, Ill.; Donald W. Laux, Dayton, Ohio

[73] Assignee: Bauer Laboratories, Inc., Chicago, Ill.

[21] Appl. No.: 361,686

[22] Filed: Dec. 22, 1994

Related U.S. Application Data

[63] Continuation-in-part of Ser. No. 971,574, Nov. 5, 1992, abandoned.

[51] Int. Cl.$^6$ ............................................. A61B 17/00
[52] U.S. Cl. ...................................... 606/1; 606/10
[58] Field of Search .............................. 606/10, 11, 12, 606/14, 15, 16, 1

[56] References Cited

U.S. PATENT DOCUMENTS

| | | |
|---|---|---|
| 4,598,311 | 7/1986 | Bellina. |
| 4,810,242 | 3/1989 | Sundblom et al.. |
| 4,870,964 | 10/1989 | Bailey, Jr. et al.. |
| 5,029,220 | 7/1991 | Juday. |
| 5,098,426 | 3/1992 | Sklar et al.. |
| 5,409,480 | 4/1995 | Uram ........................... 606/10 |
| 5,431,645 | 7/1995 | Smith et al. ..................... 606/1 |

FOREIGN PATENT DOCUMENTS

| | | |
|---|---|---|
| 0424687 | 2/1991 | European Pat. Off.. |
| 424687 A1 | 2/1991 | European Pat. Off.. |

*Primary Examiner*—Jennifer Bahr
*Assistant Examiner*—Sonya Harris-Ogugua
*Attorney, Agent, or Firm*—Wood, Phillips, VanSanten, Clark & Mortimer

[57] ABSTRACT

A surgeon's command and control (SCC) system includes an independent personal computer based electronic control unit that unifies various pieces of equipment currently found in an endoscopic surgical suite into a surgeon centered system. The system utilizes programmed software which simplifies equipment management tasks that currently encumber the surgeon and operating room staff. It enhances safety, and increases the utility of the individual pieces of equipment. The SCC hardware centers around a personal computer communicating with a sterile control panel located at the surgeon's operating station. A frame store card serves as an electronic pallet to compose and superimpose graphic images onto a surgical image transmitted from an endoscopic camera for display on a heads-up display (HUD) monitor at the surgical operating station.

22 Claims, 21 Drawing Sheets

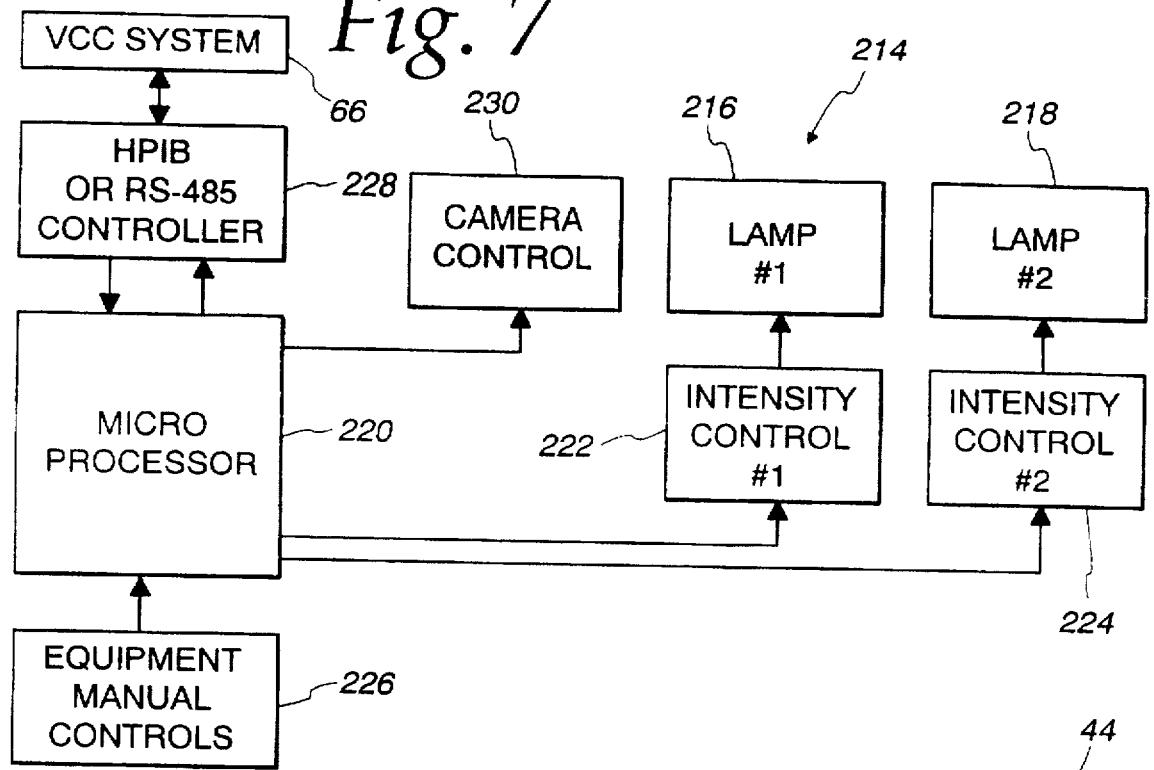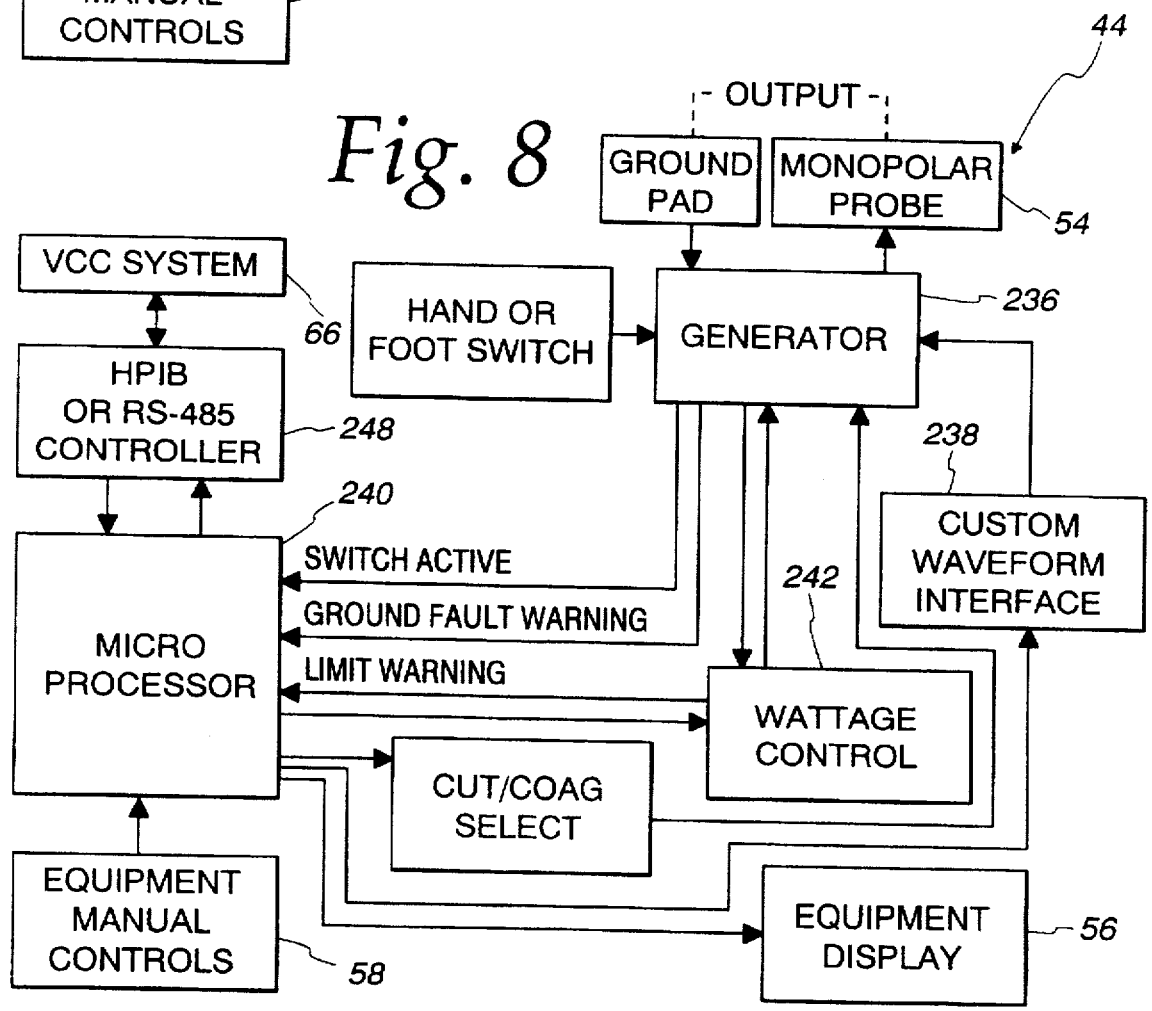

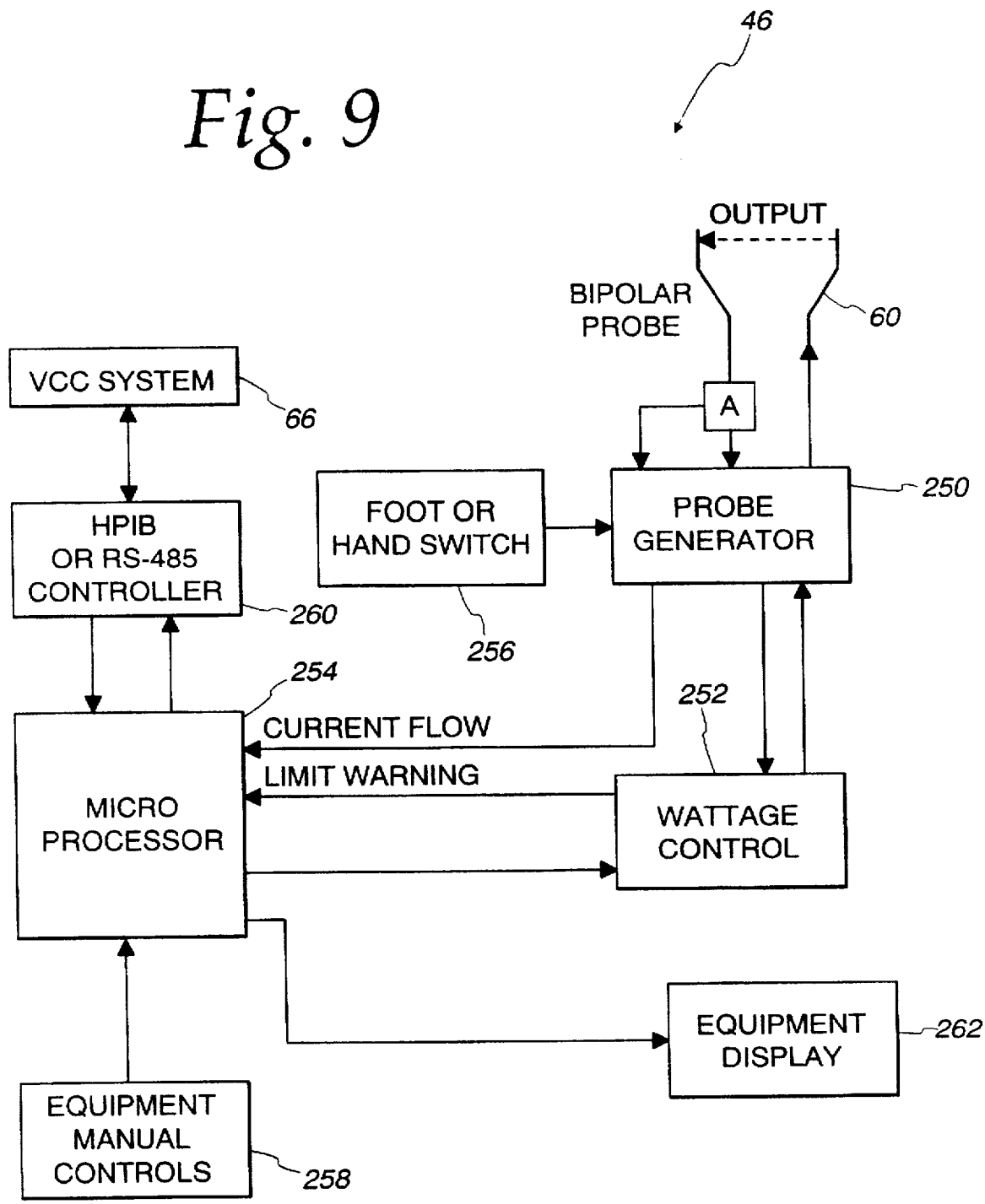

Fig. 10a
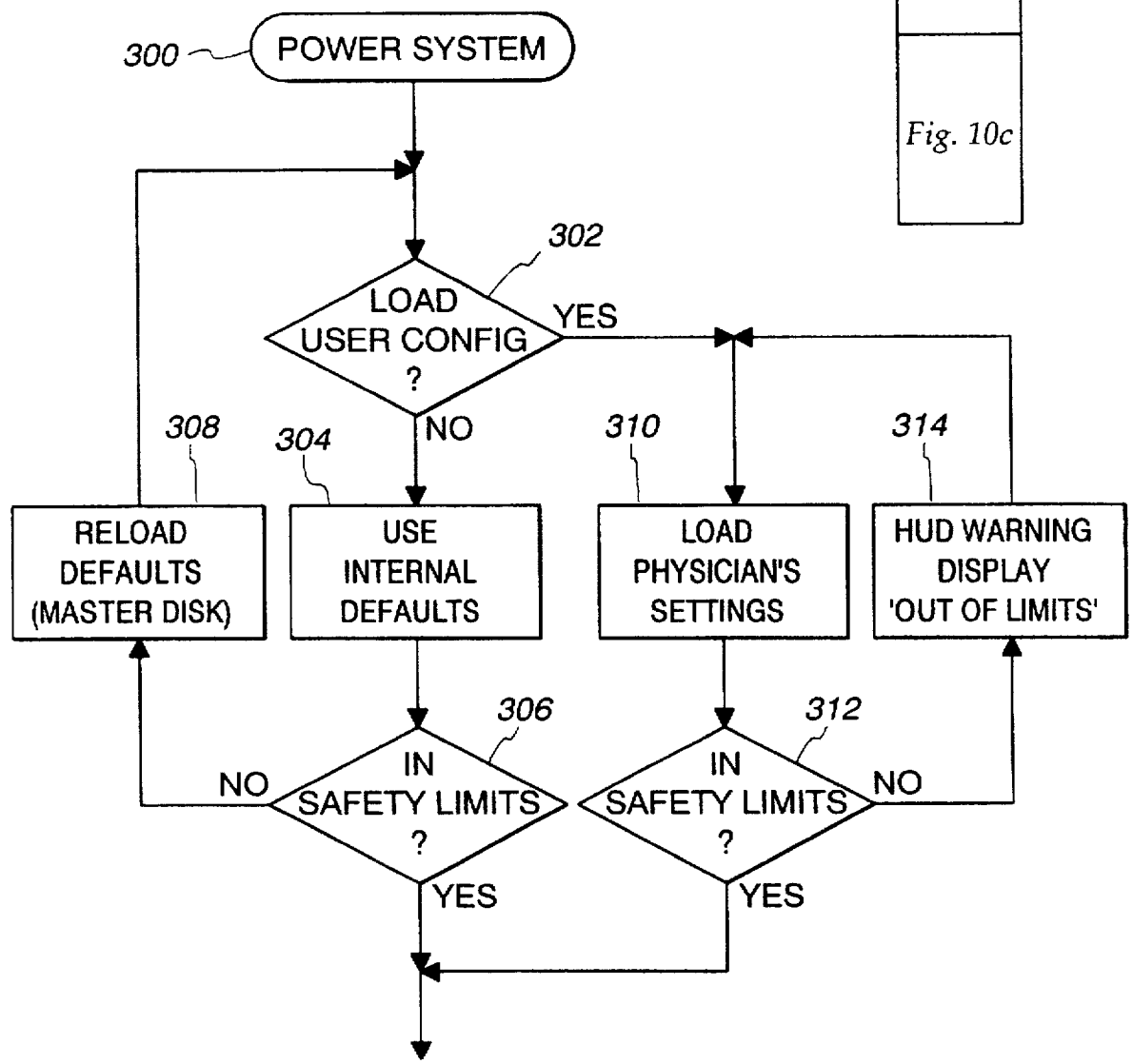
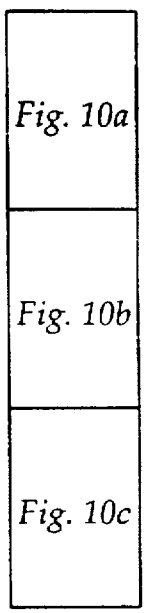

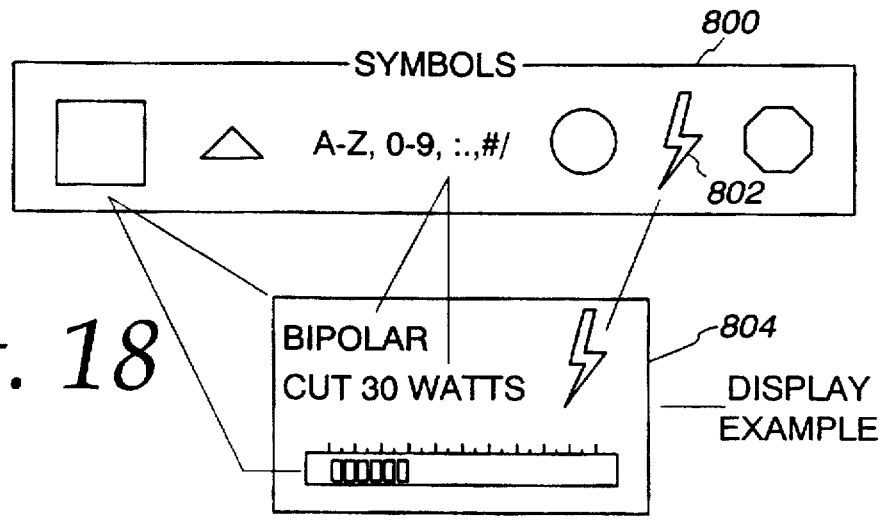
*Fig. 18*
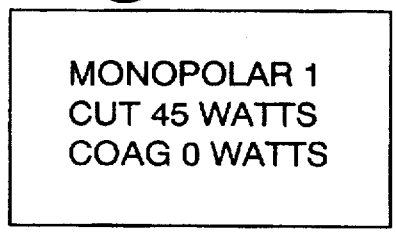
*Fig. 19a*
MONOPOLAR DISPLAY
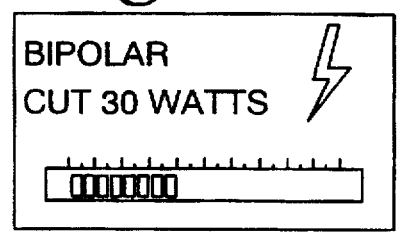
*Fig. 19b*
BIPOLAR DISPLAY
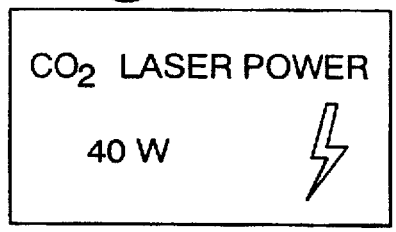
*Fig. 19c*
CO$_2$ LASER DISPLAY
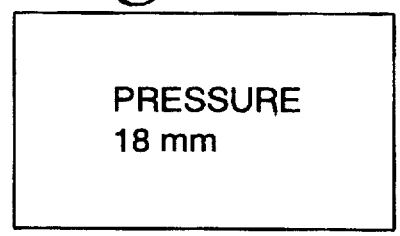
*Fig. 19d*
INTRA-ABDOMINAL PRESSURE DISPLAY
*Fig. 20*
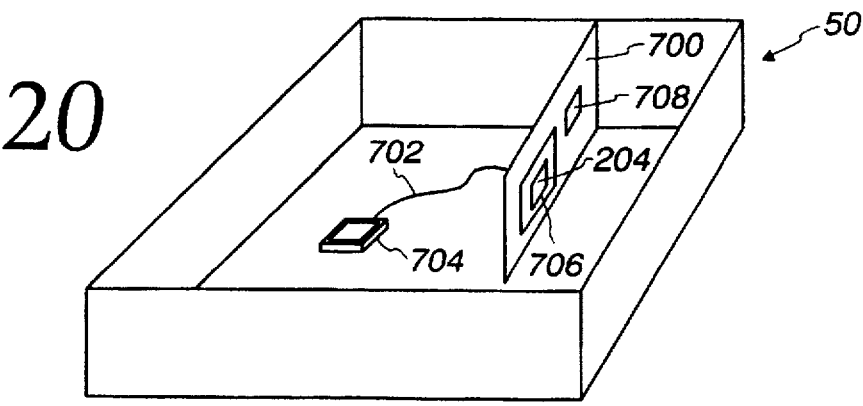

5,788,688

SURGEON'S COMMAND AND CONTROL

CROSS-REFERENCE

This application is a continuation-in-part of application Ser. No. 07/971,574, filed Nov. 5, 1992 now abandoned.

FIELD OF THE INVENTION

The present invention is directed to control of surgical equipment. Particularly, the invention is directed to a surgeon's command and control system to provide direct command and control of plural surgical equipment devices from the sterile operating environment in which the medical/surgical procedures are conducted within. The system provides increased situational awareness due to computer analysis of equipment data.

BACKGROUND OF THE INVENTION

Being a relatively young industry, endoscopic/laparoscopic surgical equipment manufacturers have focused efforts on developing individual surgical component devices. They have not recognized the requirement for creating an integrated system. The perspective from the operating room is that the introduction of additional non-integrated components of equipment will not move forward the art of endoscopic surgery, including laparoscopic surgery.

Laparoscopic surgical equipment, such as electrosurgical devices, insufflation devices, irrigation/suction pumps, and lasers, typically include a control head (or control panel) with its associated control circuitry including a central processor that connects to the electrical and electromechanical mechanisms that create a desired physical effect or act as a surgical energy source. The control head, control circuitry, and electrical/electromechanical inner workings are all housed in a single enclosure. The piece of component equipment is then connected via appropriate conduit to conduct this physical effect and deliver it to the patient through a specific endoscopic surgical instrument. The component enclosures of surgical equipment are often scattered about the operating room in non-sterile areas remote from the sterile field in which the actual surgical procedure is conducted. The surgical team, including surgeons, assistants and supporting nursing staff, must stand within this sterile field and comply with strict "sterile procedures" to insure that the patient does not become infected as a result of the surgery. The surgical instruments and items placed within this sterile field must be capable of being sterilized by either a chemical or physical means. The laparoscopic surgical instruments are sterile and are specially designed to conduct the physical effects to the patient either through the endoscope itself or associated endoscopic/laparoscopic operating ports inserted into the patient's body. Typically, the surgeon and operating assistants conduct the surgery by reference to video images of the actual site of the surgical procedure deep within the patient. This is done by connecting a small video camera to the eyepiece of the operating endoscope/laparoscope which then provides an enlarged color image from which both the surgeon and operating assistants can conduct the surgery.

The control head of each component device typically includes a visual display panel for displaying output parameters of the equipment as well as monitored inputs, and a series of buttons and switches for varying the output which drives the surgical instrument.

The surgical instruments are positioned within the sterile field proximate to a surgeon's operating station from which the procedure is performed.

As more and more pieces of surgical equipment are relied upon in surgical procedures, operating rooms are becoming more and more cluttered with equipment, and equipment is required to be placed further and further from the patient, with the control panels out of view of both the surgeon and staff.

The number of pieces of surgical equipment results in a tangle of cords and a conglomeration of equipment to be both monitored and controlled during the course of an operation. What should be a serene environment to promote concentration by the surgeon and the support staff becomes a crowded, disorganized theater with a multitude of buzzers, beeps and flashing lights enveloping the surgical team and patient. This conglomeration of equipment and need to continuously consult support staff to control equipment output and adjust equipment settings interrupts the rhythm of surgery, drawing the surgeon's attention away from the critical procedure. During a busy procedure, the difficulty in maintaining control of the various pieces of medical equipment and the difficulty in monitoring outputs could increase the possibility of errors, both in equipment output settings and slips of hand because of distractions during the surgical procedure.

Laparoscopic surgery exemplifies these problems. A laparoscopic surgeon uses a complex array of equipment, including electrosurgery, insufflation devices, suction/irrigation pumps and lasers. Each piece of equipment has specific and unique operating parameters that, if not operated uniformly, can lead to serious patient injury. The attention of the surgeon, however, must be focused upon the laparoscopic video display because of the sensitive nature of the surgical task. Thus, a surgeon cannot efficiently monitor the output settings of the various control units, both because they are scattered about the operating room and because division of attention from the video screen can have serious repercussions. Also, when a surgeon deems an adjustment of the output settings is required, the instructions must be relayed to support staff outside of the sterile field to actually adjust the equipment. This provides indirect verbal control of output to the surgical instruments. Lack of direct control can be unsafe because of possible miscommunications and can be inefficient since the attendant often is outside of the actual operating room and the surgeon and procedure must wait for the attendant's return before adjustment to the equipment can be made. Slowness in making changes and pauses in the rhythm of surgery produces economic impacts as the operating room is typically charged by the minute.

The present invention is directed to solving one or more of the problems discussed above.

SUMMARY OF THE INVENTION

In accordance with the invention a surgeon's command and control system provides a surgeon direct command and control of various surgical equipment devices in an operating room, offering to the surgeon heightened situational awareness and command of the surgical procedure.

Broadly, there is disclosed herein a surgeon's command and control system used in an endoscopic operating environment defining a surgeon's operating station at which a surgical procedure is performed with a plurality of pieces of surgical equipment. Each includes a surgical control head located in a non-sterile area remote from the surgeon's operating station and associated devices for developing an output in response to commands entered manually directly at the surgical control head for driving an associated surgical instrument located at the surgeon's operating station. The command and control center includes a surgeon's control panel operatively positioned at the surgeon's operating station. The surgeon's control panel includes display means for displaying data relating to status of the pieces of surgical equipment and input means for receiving commands entered manually. A plurality of communication interface circuits are included, one for each piece of surgical equipment, for transmitting data representing status of the associated surgical control head and for receiving remote commands for driving the associated surgical instrument. A central controller is operatively connected to each communication interface circuit and the surgeon's control panel. The central controller transmits to the pieces of surgical equipment commands entered manually on the surgeon's control panel and transmits to the surgeon's control panel status of the surgical control heads for display on the display means to provide a surgeon direct command and control of the pieces of surgical equipment located in the non-sterile area remote from the surgeon's operating station.

It is a feature of the invention to further provide an endoscopic camera electrically connected to the central controller for developing video image signals for a surgical procedure and a video monitor electrically connected to the central controller for displaying video images from the camera.

It is a feature of the invention that the central controller includes a video frame store card operatively connected between the camera and the display monitor for storing frames of video data for display on the display monitor.

It is another feature of the invention that the central controller includes means for transmitting to the frame store card status for the surgical devices for display on the video display monitor.

It is another feature of the invention that the display monitor displays video images from the camera with select fields overwritten to display status information.

It is still another feature of the invention that the central controller comprises a programmed central processing unit operating in accordance with a program stored in associated memory devices.

It is yet an additional feature of the invention that the memory devices store status and command data received by the central controller.

It is still a further feature of the invention to provide a microphone located at the surgeon's operating station and the central controller further comprises a speech recognition circuit for converting audio commands entered by a surgeon to digital signals to be transmitted to the pieces of surgical equipment.

It is still a further feature of the invention that the control panel comprises a sterile control panel.

There is disclosed in accordance with another aspect of the invention a surgical control system in an endoscopic suite including a surgeon's operating station at which a surgical procedure is performed. A piece of surgical equipment for performing a surgical procedure includes a surgical control head located at a non-sterile area remote from the surgeon's operating station and associated devices developing a variable output for driving an associated surgical instrument located at the surgeon's operating station. The piece of surgical equipment includes means for producing a signal indicative of the output to the surgical instrument and means for receiving a variable control signal, the output varying in response to variations of the control signal. A communication interface circuit transmits data representing status of the surgical control head and receives remote commands for driving the surgical instrument. A surgeon's control panel is operatively positioned at the surgeon's operating station. The surgeon's control panel includes display means for displaying data relating to the output to the surgical instrument and input means for receiving commands entered manually. A central controller is operatively connected to the communication interface circuit and the surgeon's control panel. The central controller develops and transmits to the piece of surgical equipment the variable control signal from commands entered manually on the surgeon's control panel and transmits to said surgeon's control panel data relating to the output of the surgical instrument for display on the display means to provide a surgeon direct command and control of the piece of surgical equipment located in the non-sterile area remote from the surgeon's operating station.

More particularly, a surgeon's command and control (SCC) system includes an independent personal computer based electronic control unit that unifies various pieces of equipment currently found in an endoscopic surgical suite into a surgeon centered system. The system utilizes programmable software which simplifies equipment management tasks that currently encumber the surgeon and operating room staff. It enhances safety, and increases the utility of the individual pieces of equipment. The SCC hardware centers around a personal computer communicating with a sterile control panel located at the surgeon's operating station. A frame store card serves as an electronic pallet to compose and superimpose graphic images onto a surgical image transmitted from an endoscopic camera for display on a heads-up display (HUD) monitor at the surgical operating station.

The flexibility of the HUD data display in terms of data content, format of the graphics and alphanumeric, color and pulsating video intensity changes, highlight critical information, and when operating parameters reach critical values to project information onto the video monitor using the HUD format.

The surgeon has direct control of the various surgical devices in the operating room through sterile control located at the surgeon's operating station, allowing the surgeon and assistant to make equipment adjustments without breaking sterile procedure.

The sterile control panel provides duplicate control heads for each device integrated into the SCC system so that any command input possible through adjustments made on the device's equipment box control head can be made at the sterile control panel.

The sterile control panel contains complete output displays and adjustment controls for each individual device. A surgical team member making device adjustments can change an individual device's operating parameters, configuration or power status without visually referencing the output displays found on the device's control head or the HUD monitor. The surgeon and entire staff is informed of equipment setting changes through the HUD display on the video monitor from which the surgeon is performing the surgical procedure.

The SCC system has an input signal sorting algorithm that sorts the equipment box control head and sterile control panel electronic commands to ensure the most recent confirmed command updates the device's actual hardware operating settings. A command is confirmed by an enter button located within the adjustment button cluster of both the equipment box control head and appropriate section of the sterile control panel.

State-of-the-art remote surgical equipment units incorporate a microprocessor to control its internal functions, but do not allow communication with external units. The SCC system requires that these equipment units be able to communicate externally, but redesigning existing equipment units can be very costly and take time to produce. The SCC system features a quick and easy processor emulation design method to convert existing microprocessor controlled surgical equipment for communications with the SCC system as well as to provide self diagnostics and dynamic decision status to the SCC system.

The SCC system has preset limits programmed to prevent inadvertent selection of dangerous operating power settings or equipment configurations or misuse of the equipment.

The SCC system monitors equipment operation to provide automatic recognition of certain situations and conditions that may pose an interoperative hazard. The surgeon is aware of such conditions by a warning placard appearing on the HUD information display.

The format, color and size of each information display grouping can be altered to provide optical transmission of pertinent facts, easiest visualization and minimal distraction and video screen clutter.

The SCC system monitors equipment performance and informs the surgeon of significant discrepancies through the HUD system.

The frame store electronic architecture has the ability to accommodate video image enhancing programs.

The frame store electronic architecture has the ability to accommodate laser electro-optical interrogation schemes involving both optical and video shuttering with image manipulation programs.

The system has a programmable file for each surgeon's preferred component device configuration and power settings to speed initial setup of the operating room by the support staff. When this feature is selected, the SCC system automatically configures and adjusts the hardware to the surgeon's specifications.

The SCC system provides the ability to orchestrate multiple pieces of equipment to achieve new surgical effects.

Further features and advantages of the invention will readily be apparent from the specification and from the drawing.

BRIEF DESCRIPTION OF THE DRAWING

FIG. 7 is a block diagram for a light equipment control used with the SCC system of FIG. 1;

FIG. 8 is a block diagram of an monopolar electrosurgical unit used with the SCC system of FIG. 1;

FIG. 9 is a block diagram for an bipolar electrosurgical unit used with the SCC system of FIG. 1;

FIGS. 10A–10C comprise a general flow diagram of the operation of the SCC system;

FIG. 18 is a diagram illustrating an HUD display continuous display example layout;

FIG. 19 is a diagram showing HUD symbols and a HUD display example; and

FIG. 20 is a perspective view illustrating a processor emulating concept according to the invention.

DETAILED DESCRIPTION OF THE INVENTION

Figure 1:
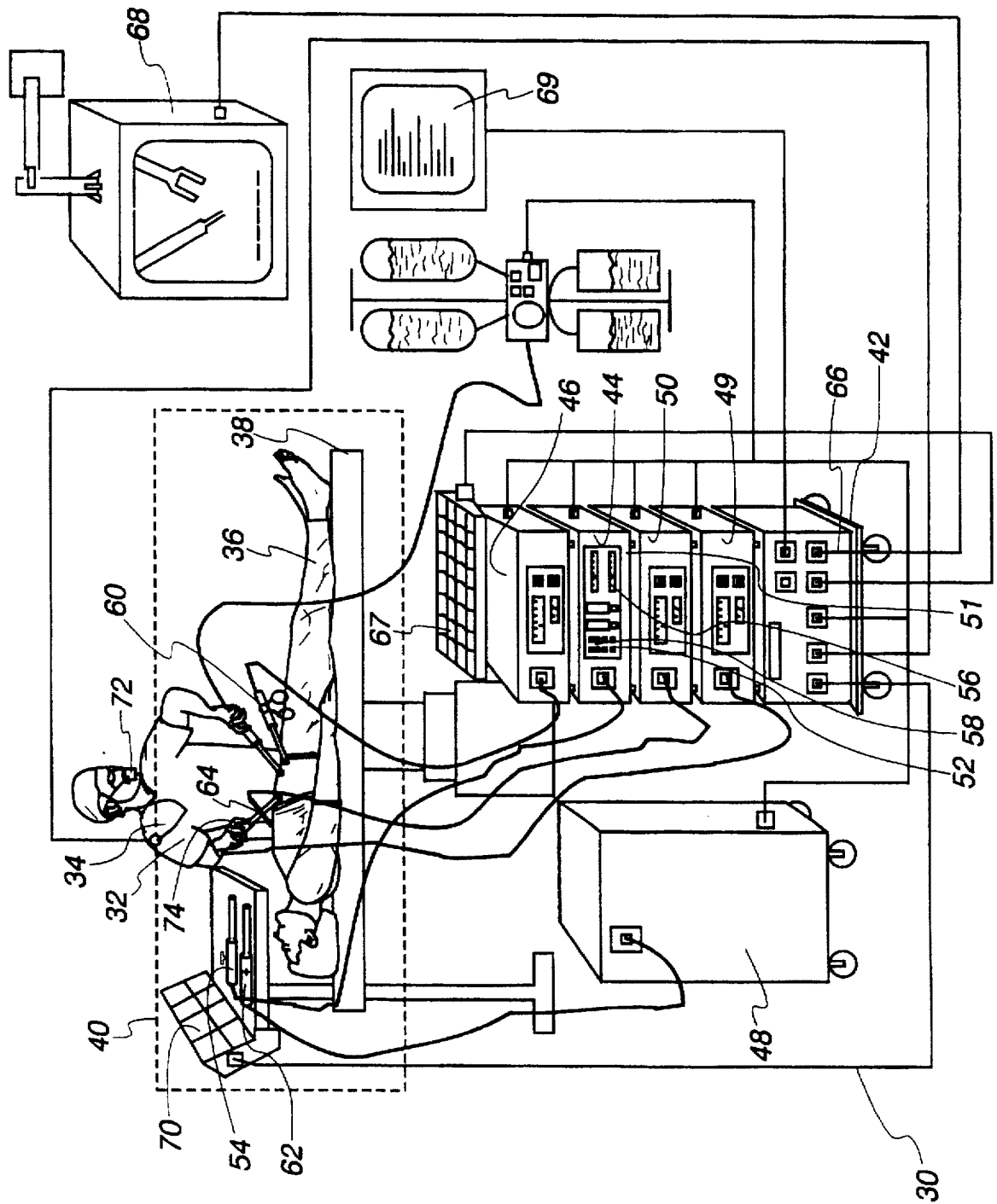
FIG. 1 is a perspective view of a surgeon performing a surgical procedure upon a patient using a surgical command and control (SCC) system according to the invention.

With initial reference to FIG. 1, an endoscopic suite in the form of an operating room 30 has a surgeon's operating station, referenced generally at 32, at which an endoscopic/laparoscopic surgical procedure is performed by a surgeon 34 on a patient 36. The patient 36 is shown lying on an operating table 38 at the surgeon's operating station 32. The surgeon's operating station 32 is located within a sterile field, shown surrounded in dashed line in FIG. 1. Although not shown, a surgical team includes not only the surgeon 34 but also support staff such as an anesthesiologist, assistants, scrub nurses and circulating technicians. The surgeon, assistants and scrub nurse would each be appropriately positioned within the sterile field about the operating table 38 as required for the particular procedure.

In accordance with the invention, a surgeon's command and control (SCC) system 40 is provided proximate the surgeon's operating station 32, as described particularly below, for providing direct command and control of operating procedures by the surgical team.

Positioned remote from the surgeon's operating station 32 is a mobile rack 42 mounting a plurality of self-contained pieces of surgical equipment. The pieces of surgical equipment which might be used in laparoscopic surgery include a monopolar electrosurgical device 44, a bipolar electrosurgical device 46, a camera control unit 49 and insufflation device 50 all mounted within the rack 42. Each of the devices 44, 46, 49 and 50 is designed to perform a particular function within the operating room. Larger pieces of self-contained surgical equipment, such as a laser device or suction/irrigation pumps, one of which is generically illustrated as 48, tend to be freestanding away from the rack 42.

The SCC system 40 is described herein for use in laparoscopic surgical procedures. The SCC system 40 can, however, be used more generally in performing various endoscopic procedures, of which laparoscopic surgery is but one type.

Illustratively, the monopolar electrosurgical device 44 includes an enclosure 51, supporting a front mounted control head or panel 52, mounted in the rack 42. The electrosurgical device 44 develops a variable output signal for driving an associated surgical instrument 54 located at the surgeon's operating station. The control head 52 includes a visual display panel 56 for displaying output parameters of the equipment as well as a series of monitored inputs. A plurality of buttons and switches, represented generally at 58, vary the output which drives the surgical instrument 54. The enclosure 51 houses internal circuitry for producing an electrical output signal to the surgical instrument 54 as controlled by the manually operated buttons and switches 58. The internal circuitry typically includes a processor based control circuit connected to a power circuit which develops the electrical output to the surgical instrument 54.

Figure 2:
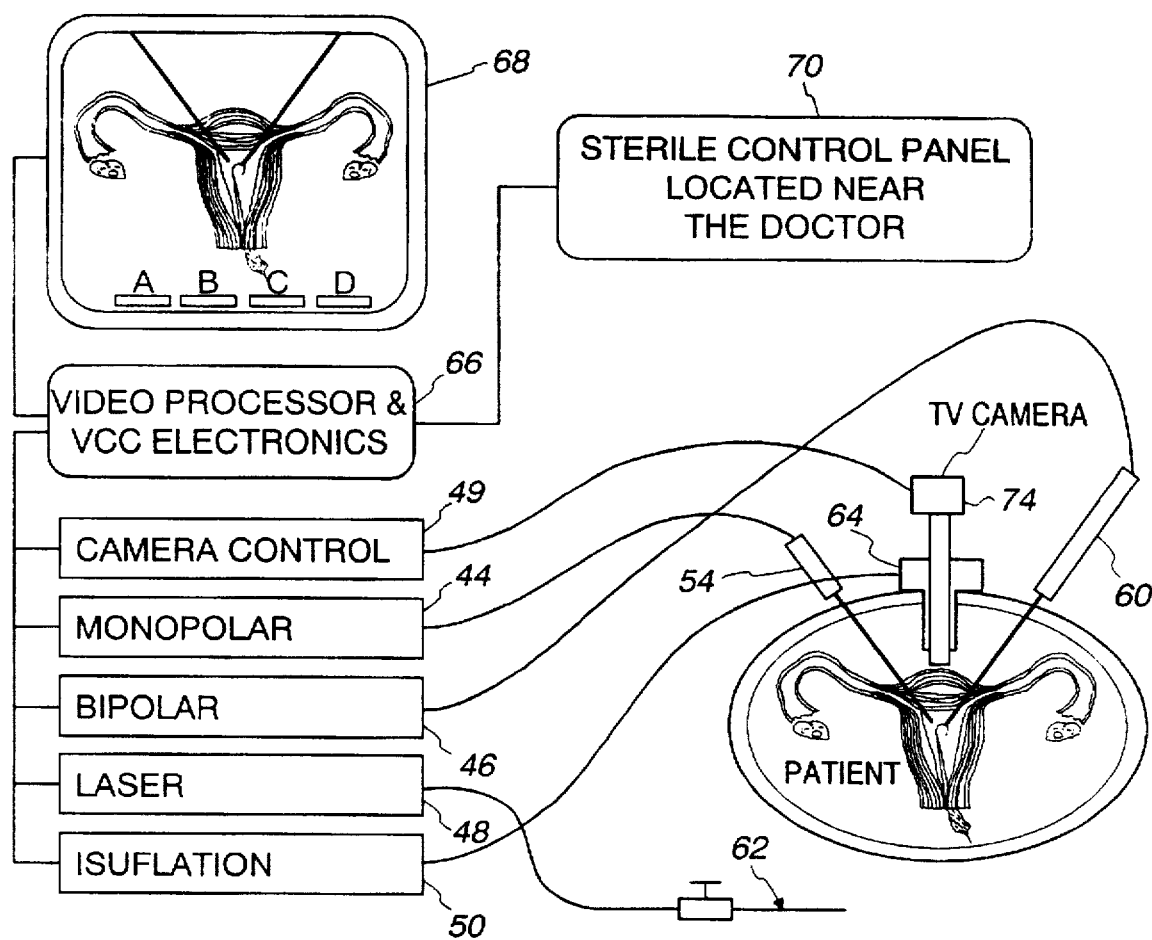
FIG. 2 is a generalized block diagram of the SCC system.

Although not specifically described, each of the pieces of surgical equipment 44, 46, 48, 49 and 50 are similar in that each includes a control head and associated devices developing an output to drive a respective associated surgical instrument 54, 60, 62, 74 and 64, see also FIG. 2. Although the pieces of surgical equipment are shown for clarity as mounted in a single rack, each is often mounted separately.

A typical endoscopic operating room includes a video surgical display monitor 68 which displays video output from an endoscopic camera 74. In accordance with the invention, the monitor 68 is used in connection with the SCC system 40. The SCC system 40 provides direct command and control at the surgeon's operating station 32 for each of the equipment control units 44, 46, 48, 49 and 50. Generally, the command and control system 40 includes a central controller in the form of an Equipment Control Unit (ECU) 66, which may be located in the rack 42, a surgeon's control panel 70, and an optional keyboard 67 and an optional programmers monitor 69. A microphone 72 may also be used. The control panel 70 and microphone 72 may be mounted to the operating table 38, a supplemental sterile instrument table placed on the patient on the operative field, attached to the anesthesia drape stand, or with a free standing stand as appropriate. All of these mounting options provide ready access to the surgical team without violation of sterile procedures.

The SCC system 40 unifies the multitude of laparoscopic surgical equipment in the operating room into a flexible surgeon-centered system. Because of the hardware and software implementation, the surgeon has complete command and control of any equipment function and receives status data on condition of the equipment. A visually interactive system is created which uses an adapted form of heads-up display (HUD) concept on the surgical video monitor 68. The video display data and static display information on the control panel 70 aid in the surgical decision making process by providing rapid, accurate feedback to the surgeon as well as to the entire surgical team.

Figure 3:
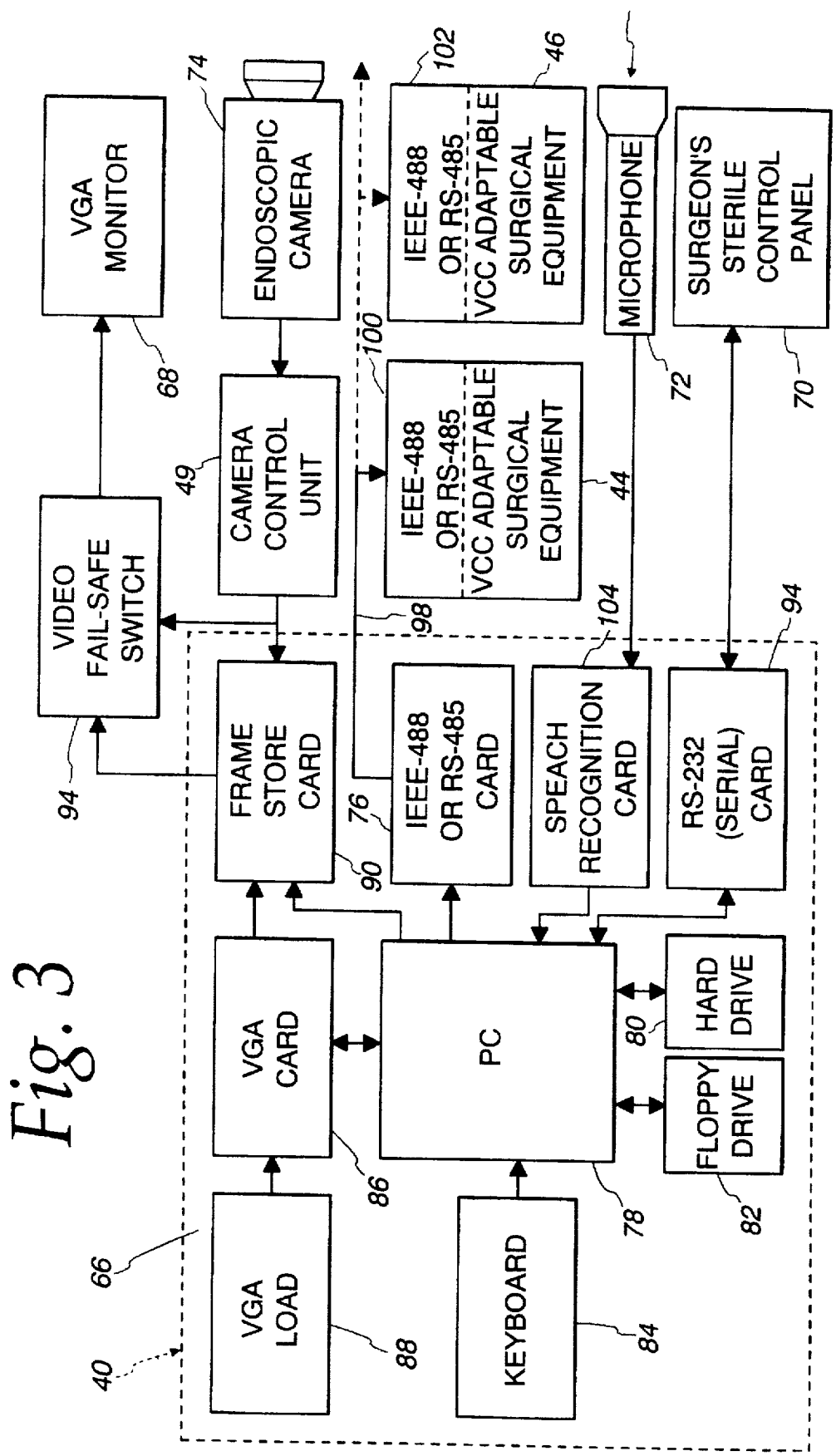
FIG. 3 is a detailed electrical block diagram of the SCC system.

Referring to FIG. 3, the SCC system 40, particularly the Equipment Control Unit (ECU) 66, is illustrated in greater detail. The heart of the ECU 66 is a personal computer system 78 which may comprise a conventional personal computer, such as a 486 DX based PC. The PC 78 includes conventional RAM and ROM memory (not shown) and conventional accessory devices such as a hard disk drive 80, floppy drive 82, keyboard 84, and Super VGA video card 86. A video frame store card 90 is used in conjunction with the standard Super VGA card 86. The VGA card 86 has a special connector location called video pass through. The frame store card 90, which also plugs into a PC expansion slot, has a cable that plugs into the video passthrough feature connector on the video card 86. The endoscopic camera 74 is connected to the camera control unit 49. The output of the camera control unit 49 is sent to the frame store card 90. The frame store card 90 is programmed to continuously or selectively "grab" a frame of video, update this frame with HUD information and send the frame out to the surgeon's monitor 68 via a failsafe switch 94. This procedure continues throughout the surgery continually updating HUD information by modifying frames of surgery video. The HUD information is received by the frame store card 90 from the PC 78 via the VGA card 86. A surgeon sees this HUD information along with video images from the endoscopic camera 74. In case of equipment malfunction, the failsafe switch 94 passes the camera control unit video directly to the surgeon's monitor 68. The VGA card 86 output connector is not used since the frame store card redirects video output to its own video connection. Since the normal video connector on the VGA card 86 is not used, a video load 88 must be connected.

A conventional serial output in the form of an RS 232 output card 94 is used for connection to the surgeon's control panel 70.

An IEEE-488 general purpose interface bus card 96 is connected to the PC 78 for connection to the surgical equipment. Alternatively, the card 96 may be an RS-485 interface card, although the HPIB interface standard is used for the sake of discussion. The card 96 provides an eight bit parallel bus with handshaking control. Thus, the equipment control unit 66 can address or select communications with one of many connected surgical equipment units. HPIB cables 98 are connected from one surgical equipment unit to another in a daisy-chain manner. This lessens cable confusion of connecting each surgical equipment unit to the back of the PC. The equipment pieces can be located at various locations within the operating room environment and the order of equipment connection is not important.

As discussed below, each piece of surgical equipment includes its own IEEE-488 HPIB controller (or RS-485 controller), see, for example, 101 and 102 in FIG. 3. These units have hardware set addresses used by the equipment control unit 66 to communication with each particular device.

Voice recognition is a progressive technology optionally incorporated in the SCC system 40 as a surgeon interface to command the system. This consists of the microphone 72 being connected via a speech recognition card 104 to the PC 78. Current voice recognition technology allows the processing of not just voice but a particular surgeon's voice. This not only enhances command and control by allowing the surgeon to concentrate on the video, but also adds a security level by allowing only certain individuals to enter commands into the SCC system 40.

Figure 4:
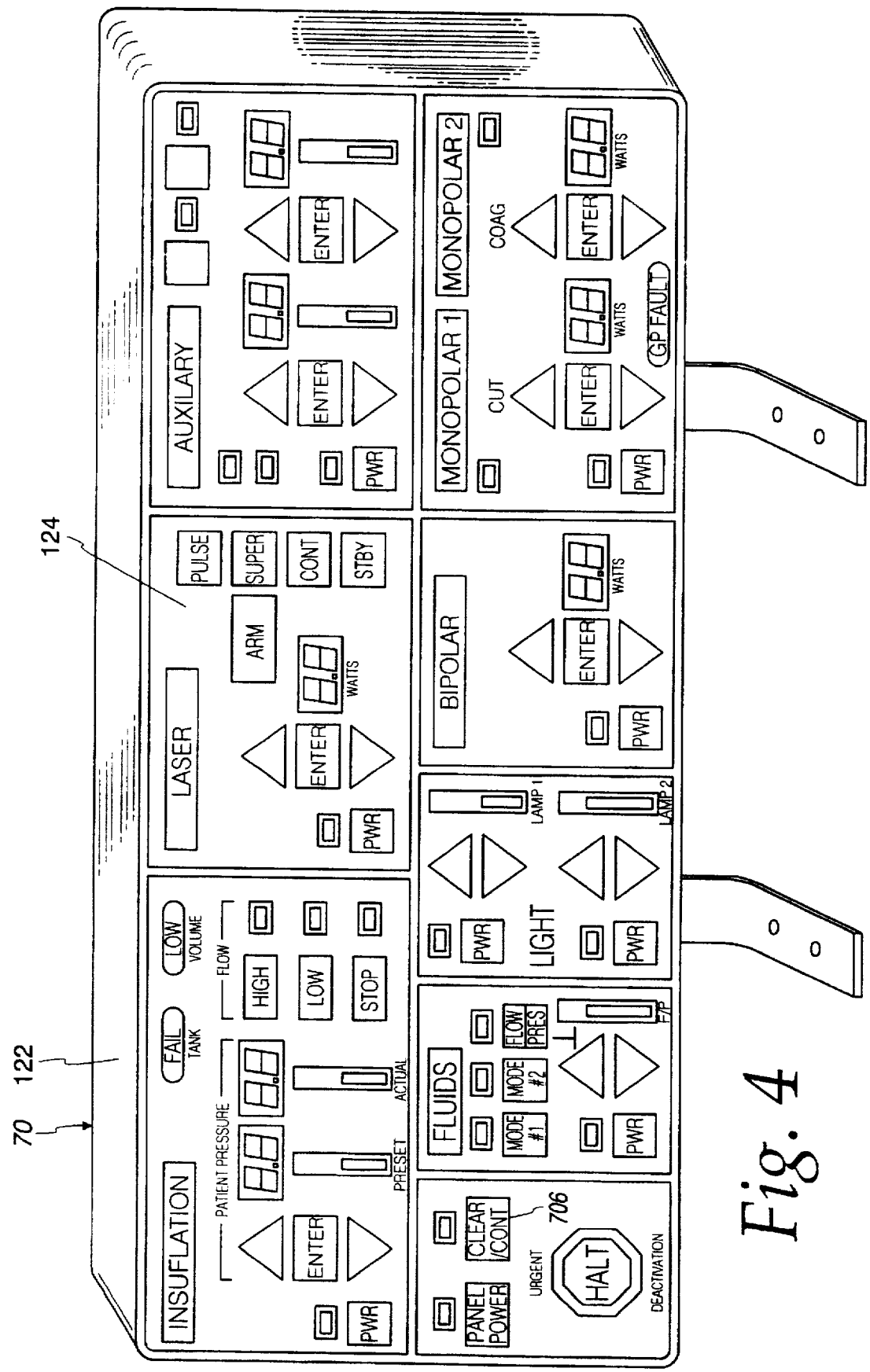
FIG. 4 is a perspective view of the surgeon's control panel of FIGS. 1 and 2.
Figure 5:
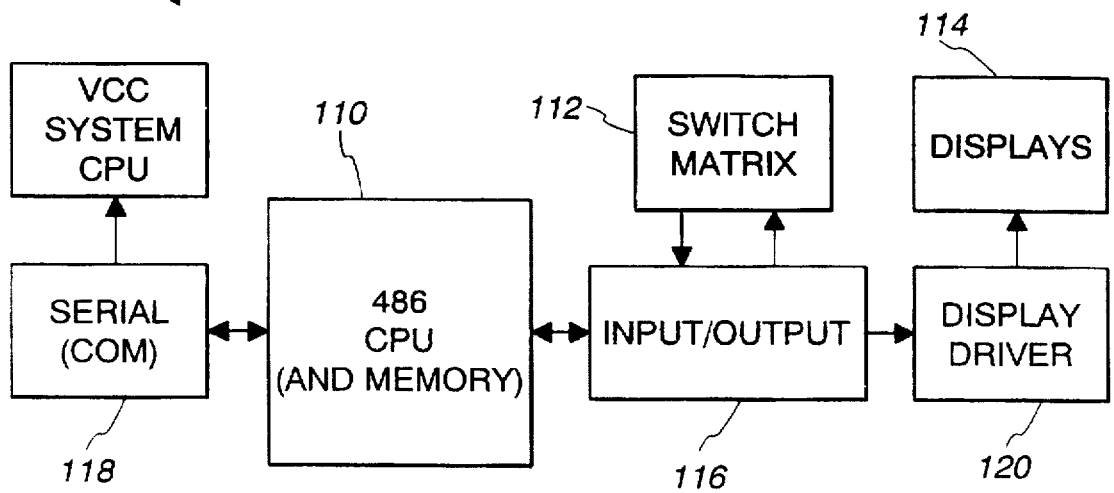
FIG. 5 is a block diagram of the surgeon's control panel of FIG. 4.

Referring to FIGS. 4 and 5, the surgeon's sterile control panel 70 includes a PC 110 consisting of an embedded 486 DX processor and memory used to service a switch matrix 112 and panel displays 114. The matrix 112 is a standard eight bit by eight bit matrix and the processor sends a sequential bit down each of the eight bit output lines. If a key is hit, it inverts the bit being sent and the change is picked up by the processor 110 on one of the eight input bits which the processor 110 monitors through an I/O port 116. The processor 110 then knows which key was entered and responds with an appropriate command sent via a serial port 118 to the ECU 66, see FIG. 3. If a display update is required, then the processor 110 sends the appropriate data to a display driver 120 which generates the proper current levels needed to illuminate the displays 114.

The control panel 70 includes an enclosure 122 of suitable material for the sterile operating room environment. A membrane switch and display panel 124 includes the switch matrix 112 and displays 114, see FIG. 5. Membrane technology fabrication produces a sealed unit construction of materials meeting stringent biomedical specifications such as toleration of chemical immersion sterilization. Additionally, the sterile control panel switch and display panel and layout meets human design specifications such as tactile feel, anti-glare features and back illumination capability, items important in the dimly lit operating room. The membrane panel may be backlit if necessary or desired.

The sterile control panel 70 duplicates the essential elements of output power setting and configuration displays found on the control unit of each individual device 44, 46, 48, and 50, see FIG. 1, so that adjustments made from the operating table positions can be done conveniently, independently, rationally and safely. The layout of the membrane switch and display panel 124 is designed with human factors of the surgeon in mind. The large rectangular switches, labeled "INSUFFLATION", "LASER", "BIPOLAR", "MONOPOLAR", and "AUXILIARY", are designed to illuminate the expanded display for that section on the HUD, as discussed below. Each switch is designed so that if any part of the raised switch surface is depressed, then the action is initiated. Triangular switches are used as an increase or decrease of particular parameter values. "ENTER" rectangular switches are used to set a value into memory and to "actuate" or transmit a command to increase or decrease the operating status of the related equipment. A bright red octagon "HALT" switch is designed into a panel as a safety feature. Actuation of the HALT switch returns each piece of surgical equipment 44, 46, 48 and 50 to its own local control at its associated control head, e.g., 52, see FIG. 1, and to maintain a stable endoscopic environment which includes adequate illumination, video image, and insufflation to provide the surgeon visualization of the operative field. This would also operate the video frame store card 90 and video switch 94 to direct raw camera output from the camera control unit 49 directly to the surgical monitor 68. All other switches control mode functions and power to remote surgical equipment. Many of these switches are co-located with a small red indicator display that reflects whether the mode or power is on or off. All numerical indicators are seven segment 0.5 inch red high intensity displays. Alternatively, liquid crystal displays with backlighting capability could be used. Bar graph displays are used to reflect percentage increase/decrease as in the light control areas as well as the insufflation preset and actual display. These indicators are ten segment, high density display units. Multiple displays indicate warnings and are composed of a series of high intensity, discrete red LED's. As "GP FAULT", "OVER PRESSURE", and "LOW VOLUME" warnings are important and warrant immediate attention by a surgeon, they are designed in software to blink on and off.

Each sectioned area within the panel 124 is isolated from other areas to separate commonalities of the switches. The panel control areas consist of panel power, clear/cont and halt switches. All other sections pertain to a particular remote surgical equipment interface. For example, the insufflation area and all switches within, are the actual controlling interface to the remote insufflation unit connected on an IEEE-488 interface, discussed above.

The actual functionality of the particular membrane switches is discussed below relative to flow diagrams for operation of the particular units.

The particular membrane panel 124 illustrated herein is designed for use with particular pieces of surgical equipment. As is apparent, the exact configuration of the panel 124 depends on the particular devices used according to surgical procedures performed. The panel 124 includes an "AUXILIARY" block for interfacing with additional pieces of equipment not described herein. The AUXILIARY block includes switches, LED's and raised surfaces to provide a generic area on the panel 124 capable of accommodating a variety of different surgical instruments. The programmed software dictates what functions of the equipment is represented by the different switches and LED outputs. The appropriate buttons and displays could then be labeled with a transparent tape and lettering. Such a method allows the light and so forth to shine through the transparent tape but highlight the lettering. Areas not used to control the designated surgical equipment would be blocked over with an opaque tape. In such a fashion, the AUXILIARY block could be adapted to any conceivable piece of equipment that the surgeon wants to interface into the SCC system 40.

Each of the remote surgical equipment pieces used is microprocessor controlled to service an HPIB controller, manual switch entries, displays and other processes, as described below. The HPIB controller on each is set for a specific address and when the equipment control unit 66 sends a command to a particular address, the addressed HPIB controller passes the command to its associated processor. The associated processor then decodes the command and responds by controlling electronic and electromechanical components within the device. If a mode is changed at the devices control head or a warning sensor is detected, then the processor responds by controlling the associated electronic and electromechanical components and encoding a command and sending it to the HPIB controller, which sends it out for the equipment control unit 66 to receive and process.

To process these commands, or to communicate back to the SCC system on its status condition, surgical equipment units must be microprocessor controlled and contain communications capabilities. A feature of the SCC system is a processor emulation interface capability to transition existing processor controlled surgical units to not only provide communications capabilities, but to also provide diagnostic and decision algorithm status to the SCC system.

The processor emulation concept involves the insertion of a small circuit card 700 into the surgical unit, such as the unit 50, see FIG. 20. The original central processing unit or microprocessor 204 that was used in the surgical unit 50 is removed and a cable 702 from the inserted card 700 plugs into its socket 704. The microprocessor 204 is then plugged into a socket 706 on the added circuit emulator card 700. In effect, this returns all normal functions back to the unit since it uses its original microprocessor that has been relocated to the added processor emulation card. The processor emulator card 700 in addition contains "buffer" circuits 708 which interface the microprocessor to the HPIB or RS-485 external interface circuit (which the original unit did not contain). The original memory in the surgical unit is re-programmed to allow input and output communications through the newly added interface circuit for remote communications.

The processor emulation card can be designed to accommodate any processor used to control existing surgical equipment. The emulation concept holds true for any processor since the key is in the reprogramming of the processor's memory.

In addition to reprogramming the surgical unit for external communications, software algorithms may be added to provide self diagnostics or to evaluate dynamic conditions and send appropriate status to the SCC system through the added input/output circuitry.

In a given piece of equipment, multiple sensors monitor the processes of each subcomponent so that the control CPU chip can send the appropriate commands to control the equipment's inner workings. The SCC HPIB boards plug taps into each component device's control CPU chip's multipin mounting and therefore the SCC has access to the raw sensor data from the equipment's inner workings for analysis. The SCC software compares the sensor data to the manufacturer's specifications and will identify components whose performance approaches or fails to meet minimum standards. As a specific subcomponent fails, the entire component is affected and the various sensors document a specific pattern that is characteristic for the particular problem. The SCC's analytic software recognizes various failure patterns in order to provide a timely and specific diagnosis of the problem. The surgeon and staff are informed by a message or warning placard on the HUD display. The SCC's computer-based analysis speeds the correction process since the SCC is monitoring, testing and troubleshooting potential malfunctions continuously. Cross-references command signals from the CPU to sensor feedback information enables the SCC to monitor actuation times of mechanical subcomponents of mechanical devices such as insufflators or irrigation/suction machines. If the internal performance of the equipment meets specification but the end performance is substandard then the SCC can direct the surgeon to look for external problems such as leaks in the tubes and connection leading to the patient. Similarly, an SCC analysis of the electrical current dynamics of a bipolar ESU in operation would allow localization of a short in the system to the cord, the Kleppenger paddles or the ESU. These examples illustrate the usefulness of having programmable computer analysis of the surgical equipment's performance and inner workings.

Figure 6:
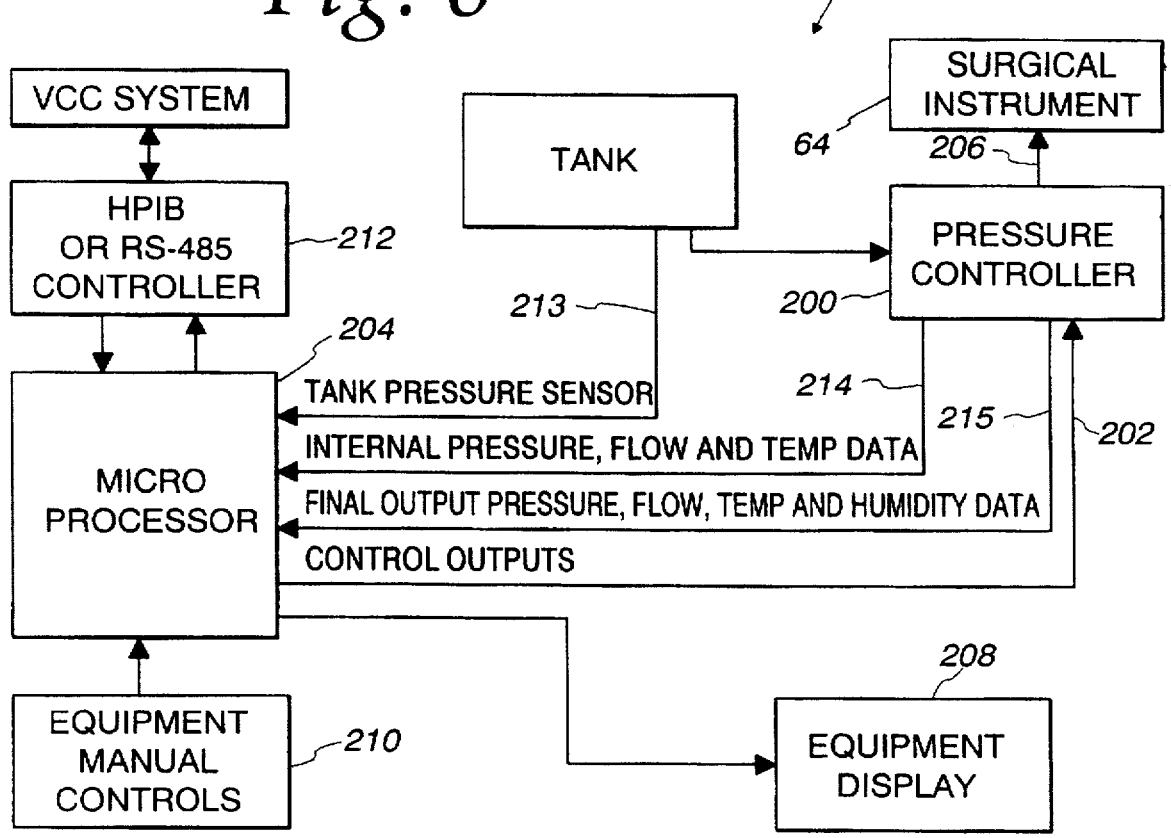
FIG. 6 is a block diagram for an insufflation unit used with the SCC system of FIG. 1.

A block diagram of a typical remote insufflation unit 50 is illustrated in FIG. 6. A high pressure gas storage cylinder (or tank) connected to a pressure controller 200 which is controlled by a control signal on a line 202 from a microprocessor 204. The final physical output of the pressure controller is low pressure gas at a specific flow rate, temperature and humidity that flows through a small pressurization line 64, see also FIG. 1, to an endoscopic operating port and into the patient. To achieve the desired safe final output, the pressure controller 200 decreases the pressure and regulates the gas flow through a series of step down pressure regulators, electromechanical valves, a low pressure storage reservoir, humidification devices, and warmers. To control the internal processes of the pressure controller 200, multiple pressure, temperature and flow sensors are placed at key locations so that the controlling microprocessor 204 can make the appropriate commands to the various internal mechanisms of the pressure controller 200. Typically, a pressure sensor, represented by a line 213, monitors tank pressure which causes a low pressure warning if tank pressure falls below a predetermined level, indicating the impending need for a new tank. A second set of sensors, represented by a line 214, monitor the gas pressures, temperatures, flow rates, and humidity of the high pressure gas from the tank processed into the desired output. A third set of sensors, represented by a line 215, monitor the final output pressure, flow rate, temperature, and humidity to ensure that the levels are safe and as desired. Recognized significant deviations in the final output cause warning messages to be generated at the microprocessor level or the ECU level. (As is apparent, the specific conditions monitored depend on the manufacturer of the particular insufflator.) The microprocessor 204 operates an associated equipment display 208 and equipment manual controls 210 on its control head. Normally, the pressure control 200 is controlled in accordance with manual commands entered by the manual controls 210 and the equipment display 208 displays status information from the microprocessor 204. An HPIB controller 212 connects the microprocessor 204 to the ECU 66, as discussed above.

Referring to FIG. 7, a block diagram illustrates a light equipment control 214 for controlling operation of lamps 216 and 218. This unit includes a microprocessor 220 controlling the lamps 216 and 218 via intensity control circuits 222 and 224, respectively, based on either a manual switch change at a local control 226 or a command via an HPIB controller 228 from the ECU 66. A camera control 230 allows camera remote control operation, such as auto shutter control and auto F-stop control, from the ECU 66.

Referring to FIG. 8, a block diagram illustrates a typical monopolar electrosurgical unit 44 which uses a surgical instrument 54, which may comprise a monopolar probe, scissors, or needle tip, and a ground pad 234 to create proper current loop needed in the electrosurgical process. A generator 236 is the control for the instrument 54. The generator 236 sets up the actual waveforms for the cutting effects the surgeon desires. If a special waveform is desired, a custom waveform interface 238 selects the custom waveform stored in the generator 236. These waveforms are selected by commands decoded by a processor 240. The generator 236 is controlled via a wattage control 242 controlled by commands decoded in the microprocessor 240. If predetermined limits are reached, then a limit warning is sent back to the processor 240 for command encoding. The surgeon presses a hand or foot switch 244 for actual activation of the connected surgical instrument 54. Actual commands are manually entered using local manual controls 58, see FIG. 1, to the microprocessor 240 or remotely via an HPIB controller 248 from the ECU 66. The equipment display 56 provides local status information at the control unit 44.

Referring to FIG. 9, the bipolar electrosurgical unit 46 includes the surgical instrument 60 in the usual form of a probe having two poles, one for sending current and the other for return. The probe 60 is controlled from an ESU generator 250 via a wattage control 252 connected to a microprocessor 254. The probe 60 allows current to be isolated to a small area of tissue and returned within the same probe. As in the monopolar unit 44, a hand or foot switch 256 activates current flow. The microprocessor 254 receives local commands manually on controls 258 or remotely via an HPIB controller 260 from the ECU 66. Local equipment displays 262 illustrate status information for the bipolar unit 46.

Following is a series of flow charts illustrating programs implemented in the SCC system processor 78 as well as the processors of the individual pieces of surgical equipment.

Figure 10B:
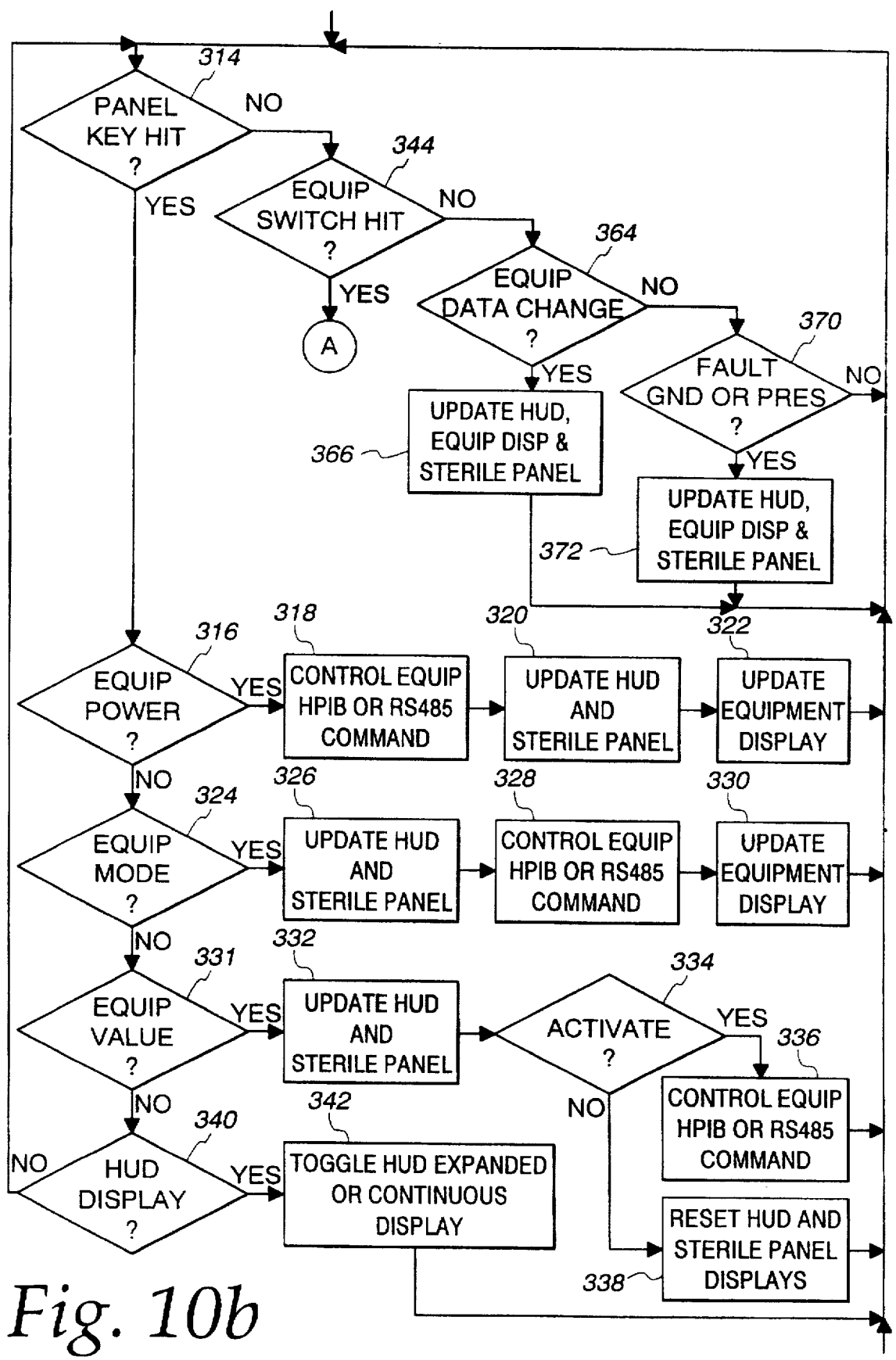
Figure 10C:
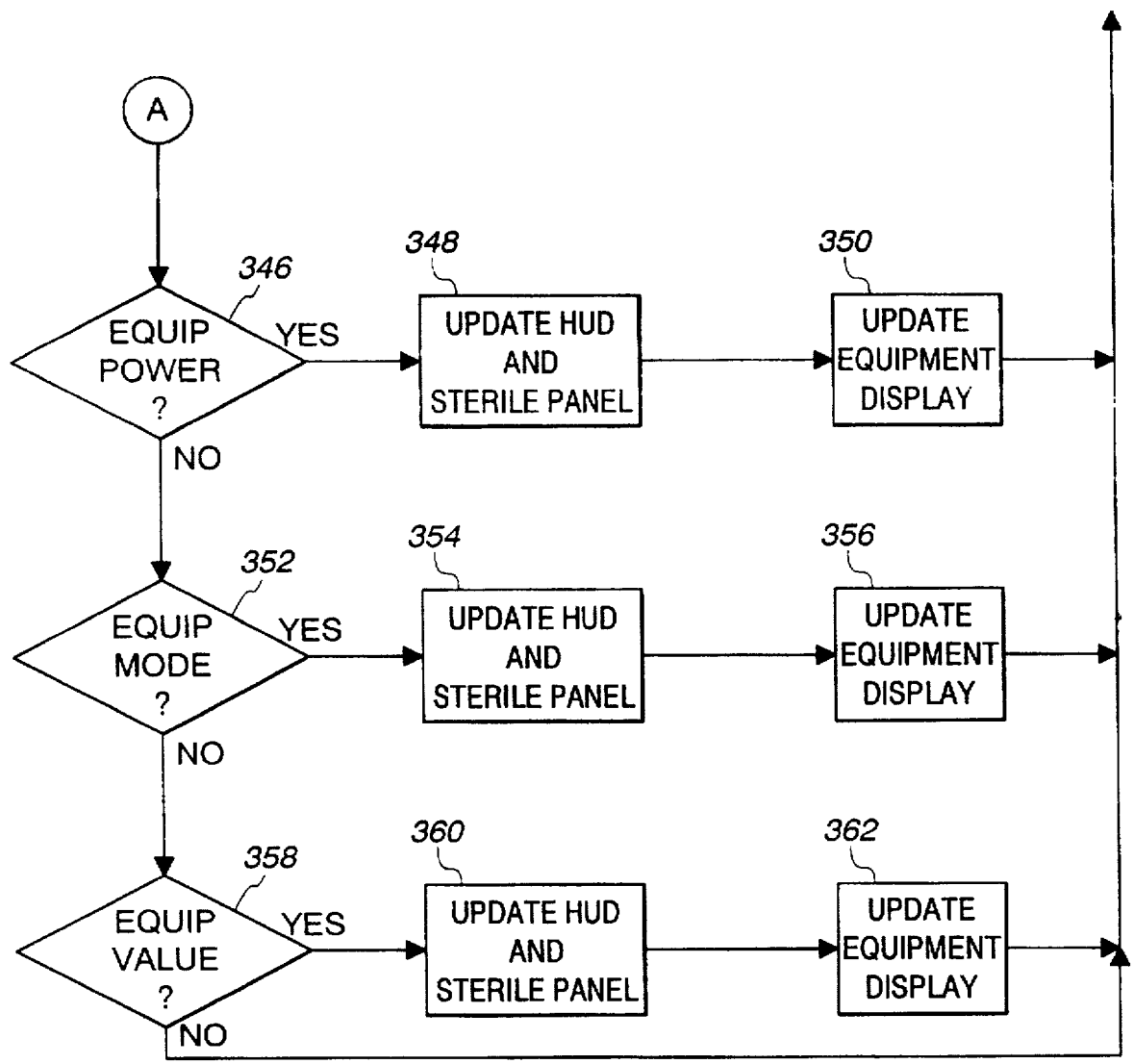

FIGS. 10A-10C represent a flow chart of the SCC system 40. Particularly, the flow charts of FIGS. 10A-10C represent software operating in both the ECU processor 78, see FIG. 3, and the sterile control panel processor 110, see FIG. 5, to gain the advantage of showing how the system works in unison. FIGS. 10A-10C illustrate general system operation, while following flow charts illustrate specific examples of equipment control to show the unique features of the SCC system 40.

With initial reference to FIG. 10A, power is supplied to the system at a node 300. A decision block 302 determines if a user configuration is loaded. The surgeon has the option of using preset system default settings or loading personalized settings. If no configuration is loaded, then internal defaults are loaded at a block 304. A decision block 306 determines if the internal defaults are within safety limits. The software has strict preset limits that are checked against defaults to ensure that the limits are not exceeded. As will be appreciated, the internal defaults can be altered by a system user and stored. This check makes sure that the system user does not exceed safe limits. If there is an attempt to exceed safe limits, then the user is prompted to re-enter default values at a block 308 until they are within the established safe limits of the equipment.

If the surgeon decides to enter in personalized settings, as determined at the decision block 302, then the position settings are loaded at a block 310. These physician settings could be stored on a floppy disk, hard disk, or internal computer memory. A decision block 312 then determines if the settings are within safety limits. If not, then a warning that the settings are out of limits is provided on the HUD display of the monitor 68 at a block 314 and control returns to the block 310.

Initial defaults and the surgeon's personalized settings are similar except that initial settings are more generic for multiple surgeon's desires.

Once it is determined that the settings are within safety limits, at either a decision block 306 or decision block 312, then control proceeds to FIG. 10B to continuously loop to service either a key entry, an equipment change or warning. Initially, a decision block 314 determines if the surgeon has depressed a key on the membrane panel 124. (At setup, any default or personalized settings within safety limits are entered and then acted on as though commands were entered manually by a surgeon depressing a key on the membrane panel.) If so, the logic flow leaves the main loop temporarily to service the entry. A key entry by the surgeon results in one of four results. A decision block 316 determines if an equipment power toggle was selected. If so, then a HPIB interface command is generated at a block 318 to be sent to the appropriate piece of surgical equipment. This equipment is then turned on or off by its internal processor, which decodes the command. The HUD and sterile panel displays are then updated at a block 320 and the equipment display is updated at a block 322. Control then loops back to the decision block 314.

If a power toggle switch was not selected at the decision block 316, then the software checks to see if an equipment mode switch was selected at a decision block 324. If so, then the HUD display and sterile panel are updated at a block 326, the HPIB command is transmitted at a block 328 and the equipment display is updated at a block 330. Control then returns to the decision block 314.

If a mode switch was not selected, at the decision block 324, then a decision block 331 determines if a particular value was changed. If so, then the HUD display and sterile panel display are updated at a block 332 and a decision block 334 determines if the particular value has been activated, as by pressing the enter key, as discussed above. The software then waits to see if the surgeon hits an enter key, if so, then the HPIB command is sent at a block 336. If not, then the HUD and sterile panel displays are reset at a block 338. From either case, the control returns to the decision block 314.

If a value change was not desired, at the decision block 331, then a decision block 340 determines if the surgeon entered a HUD display changed, as by depressing one of the mode labels or equipment labels on the panel 124, discussed above. If so, then the HUD display is toggled to expanded or continuous display at a block 342. In either case, control returns to beginning of the main loop at the decision block 314.

Returning to the decision block 314, if no panel key has been hit, then a decision block 344 determines if a switch has been entered on any piece of surgical equipment, as by receiving an HPIB command from one of the pieces of equipment. If so, then control advances via a node B through a sequence of events very similar to that above for the main loop, but in the opposite direction. A decision block 346 determines if the equipment power has been changed. If so, then the HUD and sterile panel are updated at a block 348 and the equipment display is updated at a block 350 and the routine ends. If the equipment power was not changed, then a decision block 352 determines if equipment mode is changed. If so, then the HUD and sterile panel are updated at a block 354 and the equipment display is updated at a block 356 and the routine ends. If the equipment mode was not changed, then a decision block 358 determines if an equipment value was changed. If so, then the HUD and sterile panel are updated at a block 360 and the equipment display is updated at a block 362. Thereafter, the loop ends. Thus, when any such change from a piece of equipment is required, then a command is sent to the ECU 66 where the HUD display and memory are altered. The ECU 66 issues a follow on command that is sent to the sterile panel 70, where its display is updated. The equipment processor also updates its own associated equipment display on its control head. After the equipment enter key is processed, then the ECU 66 returns to its main loop at the decision block 314.

If an equipment switch was not hit, as determined at the decision block 344, see FIG. 10B, then a decision block 364 determines if equipment data has changed. This occurs if a particular equipment processor sends a command to the ECU 66 because of a change in parameter value within the surgical equipment. If there is a change, then the equipment display is updated at a block 366 and the HUD and sterile panel are updated, as is the memory, at a block 368 and the control returns to the decision block 314. If no equipment data change has occurred, then a decision block 370 determines if a warning has developed within the surgical equipment, such as a ground fault or pressure alarm. If a warning is developed within the surgical equipment, then the equipment processor sends a command to the ECU 66. The equipment display is updated at a block 372 and the HUD and sterile panel are updated at a block 374. Control then returns to the decision block 314. Likewise, if no warning occurs, as determined at the decision block 370, then control also returns to the block 314.

As mentioned above, the flow chart of FIGS. 10A–10C comprise an overview for generic system operation. The remaining flow charts describe particular implementations for the pieces of surgical equipment shown in FIG. 1 showing interaction between the SCC system 40 and the particular piece of surgical equipment. For each piece of surgical equipment, the first flow chart represents SCC control of the surgical equipment and follows the process represented in the generic SCC system flow chart discussed above. This side of the example is abbreviated and represents the types of controls that influence external equipment. The second flow chart for each piece of equipment represents a software process within the specific surgical equipment. In either case, power commands have been eliminated since they are common to all units and it is fully explained above.

Figure 11:
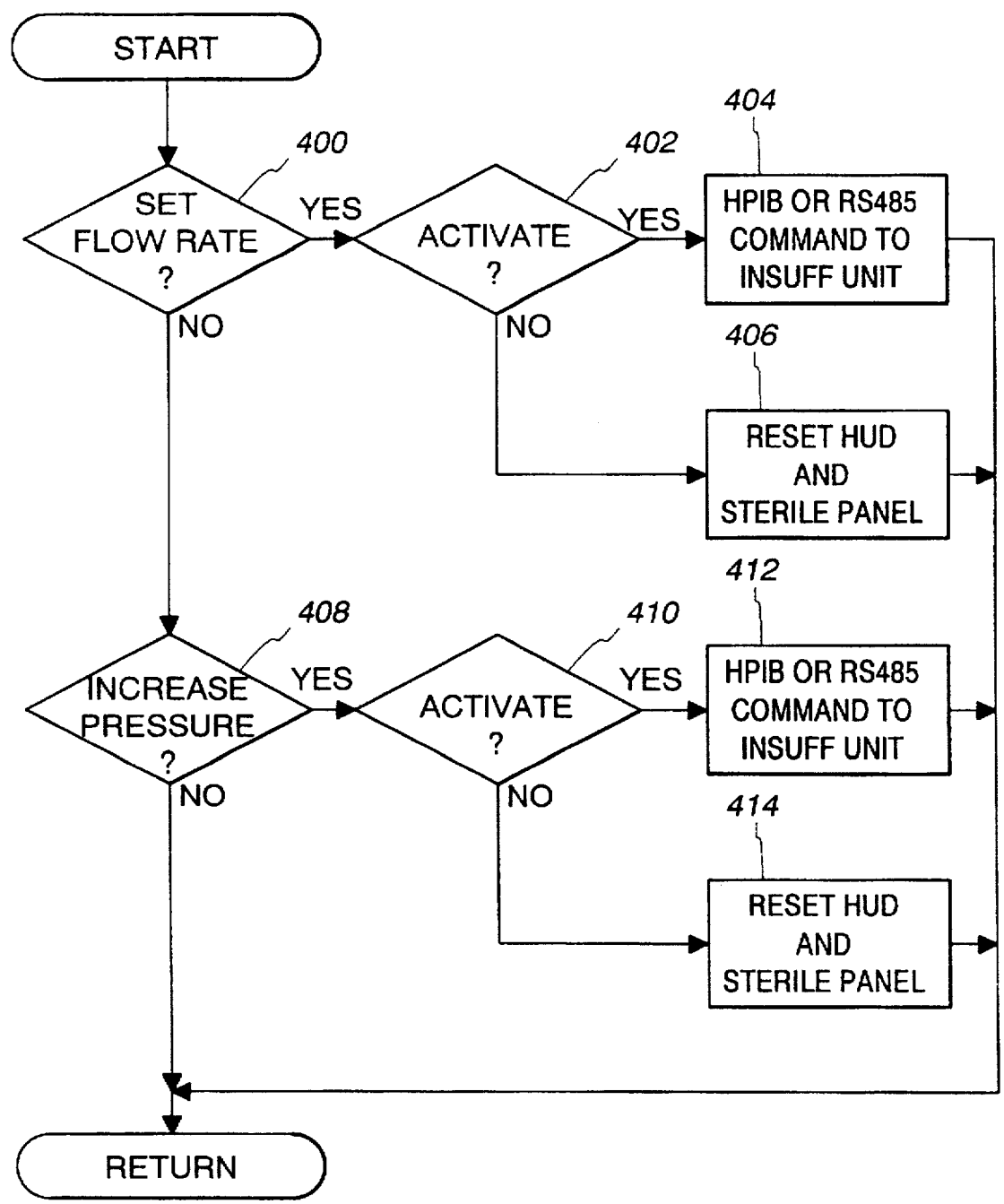
FIG. 11 is a detailed flow chart detailing control of an insufflation unit within the SCC system.

FIG. 11 illustrates a flow chart for SCC control of an insufflation unit 50, see FIG. 1. Commands can be sent to the insufflation unit to set flow rate or increase pressure. A decision block 400 determines if a change has been made on the control panel 124 to set flow rate. If so, an activate decision block 402 waits for the enter key to be pressed. If activated, then the flow rate command is sent to the Insufflation unit 50 at a block 404. Otherwise the HUD display and sterile panel 70 are reset at a block 406. If the set flow rate command was not entered at the block 400, then a decision block 408 determines if a change has been made on the control panel 124 to increase pressure. If so, an activate decision block 410 waits for the enter key to be pressed. If activated, then the increase pressure command is sent to the Insufflation unit 50 at a block 412. Otherwise the HUD display and sterile panel 70 are reset at a block 414.

Figure 12:
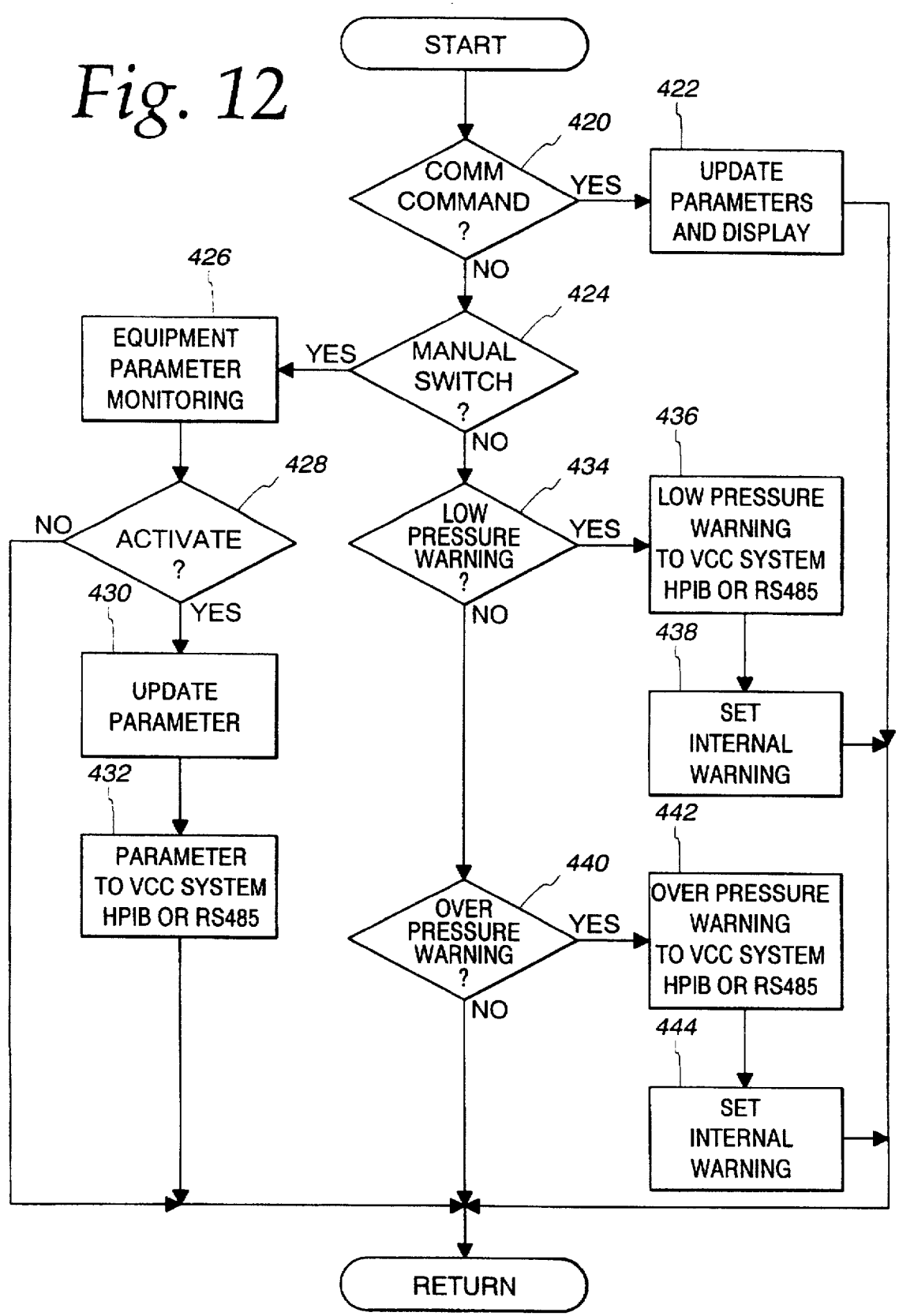
FIG. 12 is a flow chart illustration of operation of an insufflation unit.

Referring to FIG. 12, a flow diagram illustrates processing within the insufflation unit 50. The main software loop continuously services the equipment by looking for certain conditions. A decision block 420 determines if a command is received at the HPIB controller 212 for processing. In particular, such a command would be the set flow rate and increase pressure commands from FIG. 7. If there is such a command, then the processor decodes it and updates the appropriate parameters and display at a decision block 422 and then control returns to the start of the main loop. If there is no such command, then a decision block 424 determines if a manual switch has been depressed. If so, then the processor continues to look at this input at a block 426 and if activated, as determined at a block 428, updates the parameter at a block 430 and transmits the parameter to the SCC system with an HPIB command at a block 432. Thereafter, or if the command is not activated, then the system returns to the beginning of the main loop.

If a manual switch is not entered, then a decision block 434 determines if there is a low pressure warning. If so, then a low pressure warning is sent to the SCC system 40 at a block 436 and an internal warning is set at a block 438 and the system returns to the beginning of the main loop. If a low pressure warning is not present at the block 434, then a decision block 440 determines if there is an over pressure warning. If so, then an over pressure warning is sent to the SCC system 40 at a block 440 and an internal warning is set at a block 444 and the system returns to the beginning of the main loop. As is apparent, each of the warning conditions, low pressure and over pressure could be serviced simultaneously using interrupts. The flow chart illustrates the basic sequential operation of the system.

Figure 13:
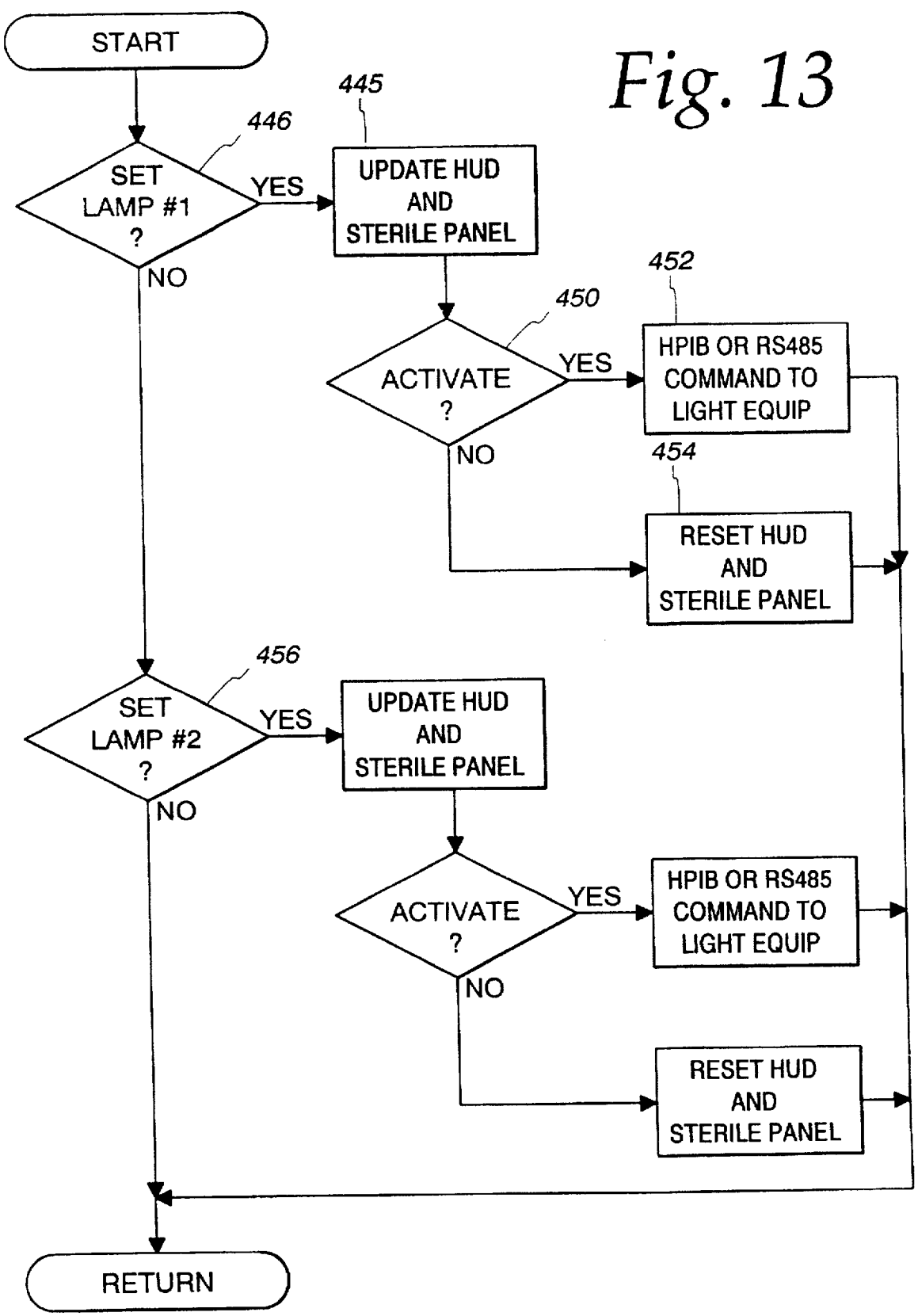
FIG. 13 is a detailed flow chart detailing control of a light unit within the SCC system.

FIG. 13 illustrates a flow chart of SCC operation for a typical light unit. If the first set lamp switch is activated at a block 446, then the HUD and sterile panel are updated at a block 448. A decision block 450 waits for the command to be activated. If so, then an HPIB command is sent to the light equipment at a block 452. If not activated within a preselected time, then the HUD and sterile panel are reset at a block 454. The control loop is similar for the second set lamp, beginning at a decision block 456. The remainder of the loop is not described.

Figure 14:
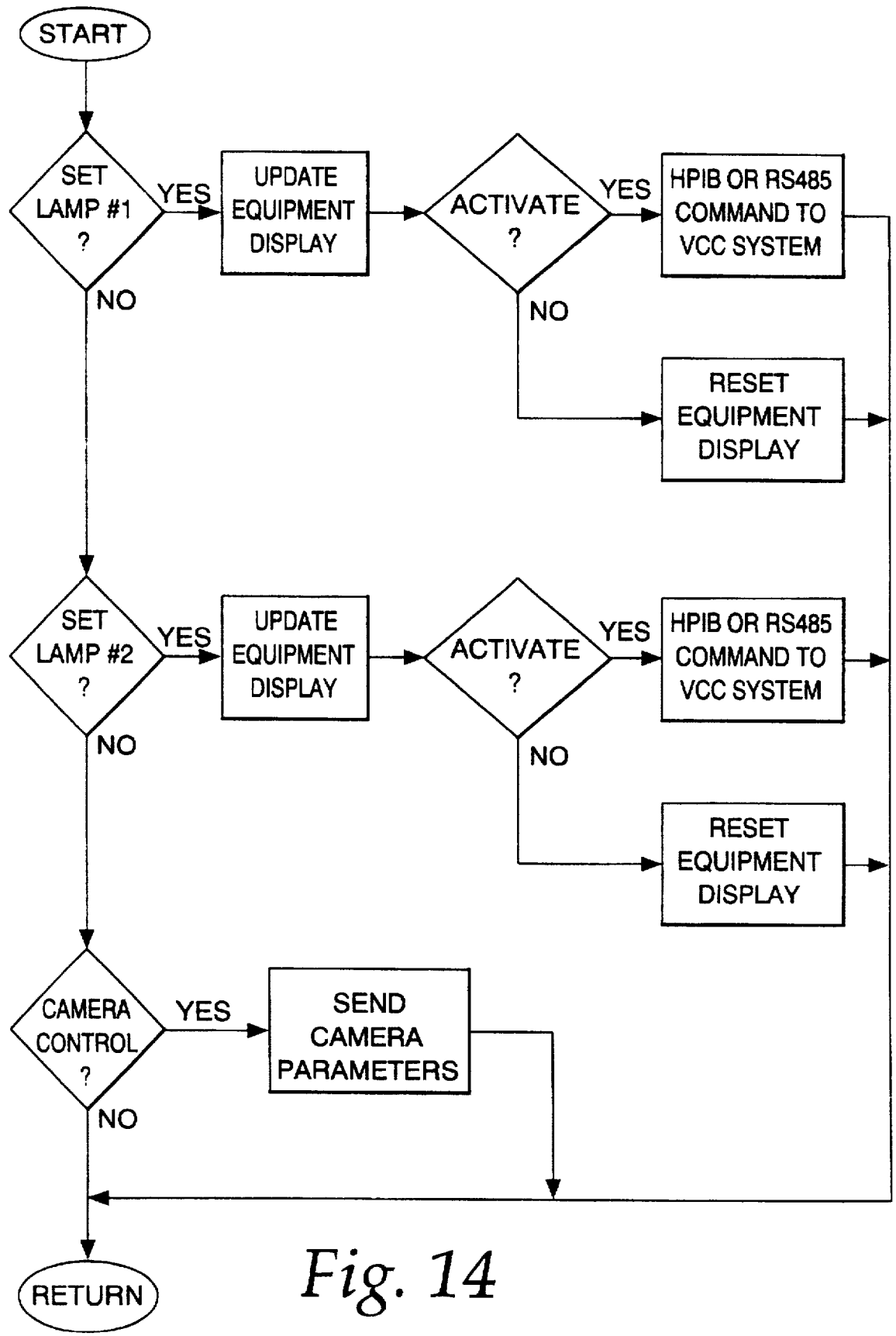
FIG. 14 is a flow chart example of a light unit.

FIG. 14 illustrates a flow chart for the process flow within the light unit itself. The process flow for both lamps 1 and 2 is exactly the same as above relative to FIG. 13 and the one chosen depends on the particular switch selected at the equipment. A cameral control option allows selecting camera parameters within the equipment.

Figure 15A:
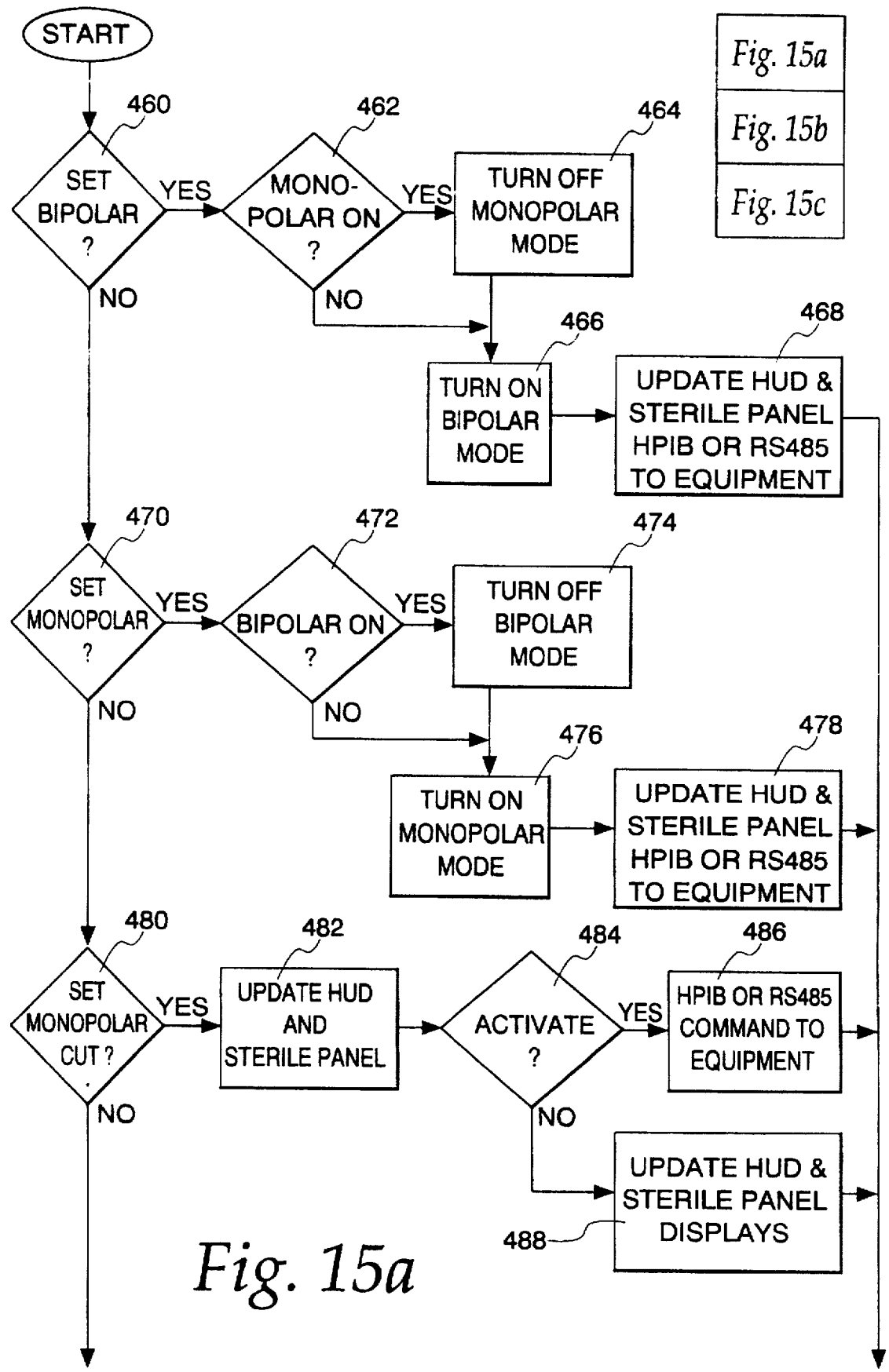
FIGS. 15A–15C are a detailed flow chart detailing control of an electrosurgical unit within the SCC system.
Figure 15B:
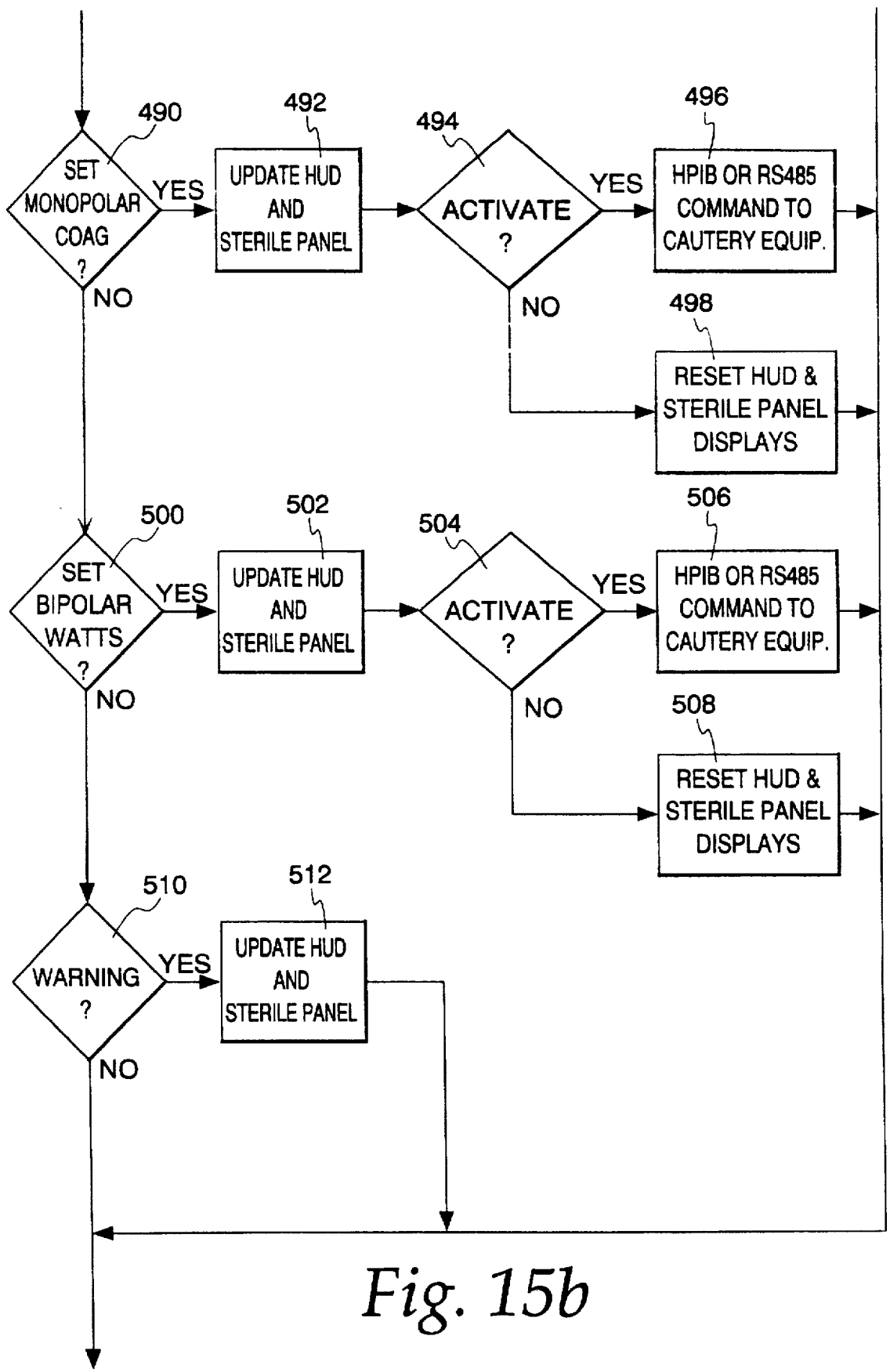
Figure 15C:
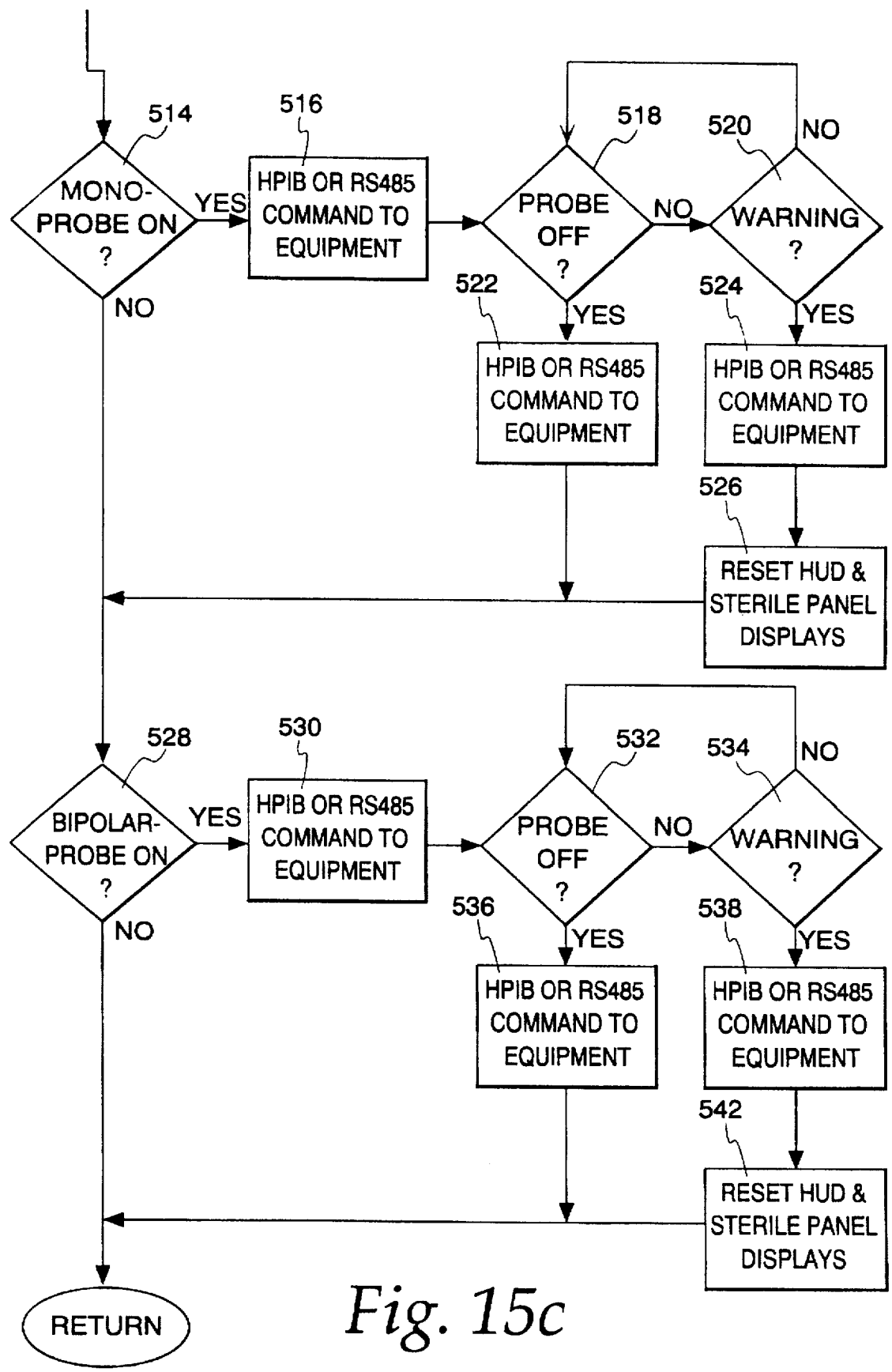

The flow chart of FIGS. 15A, 15B and 15C illustrate SCC system operation for external electrical surgical equipment, such as the monopolar electrosurgical device 44 and bipolar electrosurgical device 46, see FIG. 1. Set Bipolar and Set Monopolar are modes selected by the sterile panel 70, and when one is selected the other is turned off (if it is on). This mutually exclusive operation of the monopolar device 44 and the bipolar device 46 precludes the dangerous situation in which the surgeon has two active electrosurgical power sources in operation. The HUD and sterile panel displays are updated and a command is sent to the appropriate external equipment through the HPIB interface. Particularly, a decision block 460 determines if the command has been entered on the panel 144 to Set Bipolar on. If so, then a decision block 462 determines if the monopolar unit is on. If so, then the monopolar mode is turned off at a block 464. If not, or thereafter, then the bipolar mode is turned on at a block 466 and the HUD and sterile panel are updated and HPIB commands sent to the appropriate piece of equipment at a block 468 and control proceeds via node D to a node E of FIG. 15C, discussed below.

If bipolar mode was not set, at the decision block 460, then a decision block 470 determines if monopolar mode is set. Particularly, a decision block 470 determines if the command has been entered on the panel 144 to Set Monopolar on. If so, then a decision block 472 determines if the bipolar unit is on. If so, then the bipolar mode is turned off at a block 474. If not, then the monopolar mode is turned on at a block 476 and the HUD and sterile panel are updated and HPIB commands sent to the appropriate piece of equipment at a block 478 and control proceeds via node D to a node E of FIG. 15C, discussed below.

If monopolar mode is not set at the decision block 470, then a decision block 480 determines if Monopolar cut has been set. If so, then the HUD and sterile panel are updated at a block 482. A decision block 484 waits until the cut is activated by hitting the enter key. If so, then the HPIB command is sent to the monopolar unit 44 at a block 486. If not, then the HUD and sterile panel displays are reset at a block 488. Control then proceeds to the node E of FIG. 15C.

If Monopolar cut was not set, then a decision block 490 determines if monopolar coag has been selected on the sterile panel 124. If so, then the HUD and sterile panel are updated at a block 492. A decision block 494 waits until the command is activated by hitting the enter key. If so, then the HPIB command is sent to the monopolar electrosurgical unit 44 at a block 496. If not, then the HUD and sterile panel displays are reset at a block 498. Control then proceeds to the node E.

If the monopolar coag was not set at the block 490, then a decision block 500 determines if the bipolar wattage is set at the decision block 500. If so, then the HUD and sterile panels are updated at a block 502. A decision block 504 waits until the selection is activated as by depressing the enter key. If so, then the HPIB command is sent to the bipolar electrosurgical unit 46 at a block 506. After a timeout, then the HUD and sterile panel displays are reset at a block 508 and control proceeds to the node E.

If bipolar wattage is not set at the decision block 500, the a decision block 510 determines if a warning error has been received. If so, then the HUD and sterile panels are updated at a block 512. Otherwise, control proceeds via the node E to the flow chart of the FIG. 15C.

From the node E, a decision block 514 determines if a command is entered on the panel 124 to turn the monopolar electrosurgical probe 54 on. If so, then an HPIB command is sent to the monopolar electrosurgical unit 44 at a block 516. A decision block 518 determines if the probe is off. If not, then a decision block 520 determines if an error has occurred. If not, then control returns to the decision block 518. If the probe is off, then an HPIB command is sent to the equipment at a block 522. If an error has occurred, then an HPIB command is sent to the equipment at a block 524 and the HUD and sterile panel displays are reset at a block 526. Thereafter, or from the block 522, control proceeds to a decision block 528, which determines if the bipolar probe is to be turned on. A decision block 528 determines if a command is entered on the panel 124 to turn the bipolar electrosurgical probe 68 on. If so, then an HPIB command is sent to the bipolar electrosurgical unit 58 at a block 530. A decision block 532 determines if the probe is off. If not, then a decision block 534 determines if an error has occurred. If not, then control returns to the decision block 532. If the probe is off, then an HPIB command is sent to the equipment at a block 536. If an error has occurred, then an HPIB command is sent to the equipment at a block 538 and the HUD and sterile panel displays are reset at a block 540.

Figure 16A:
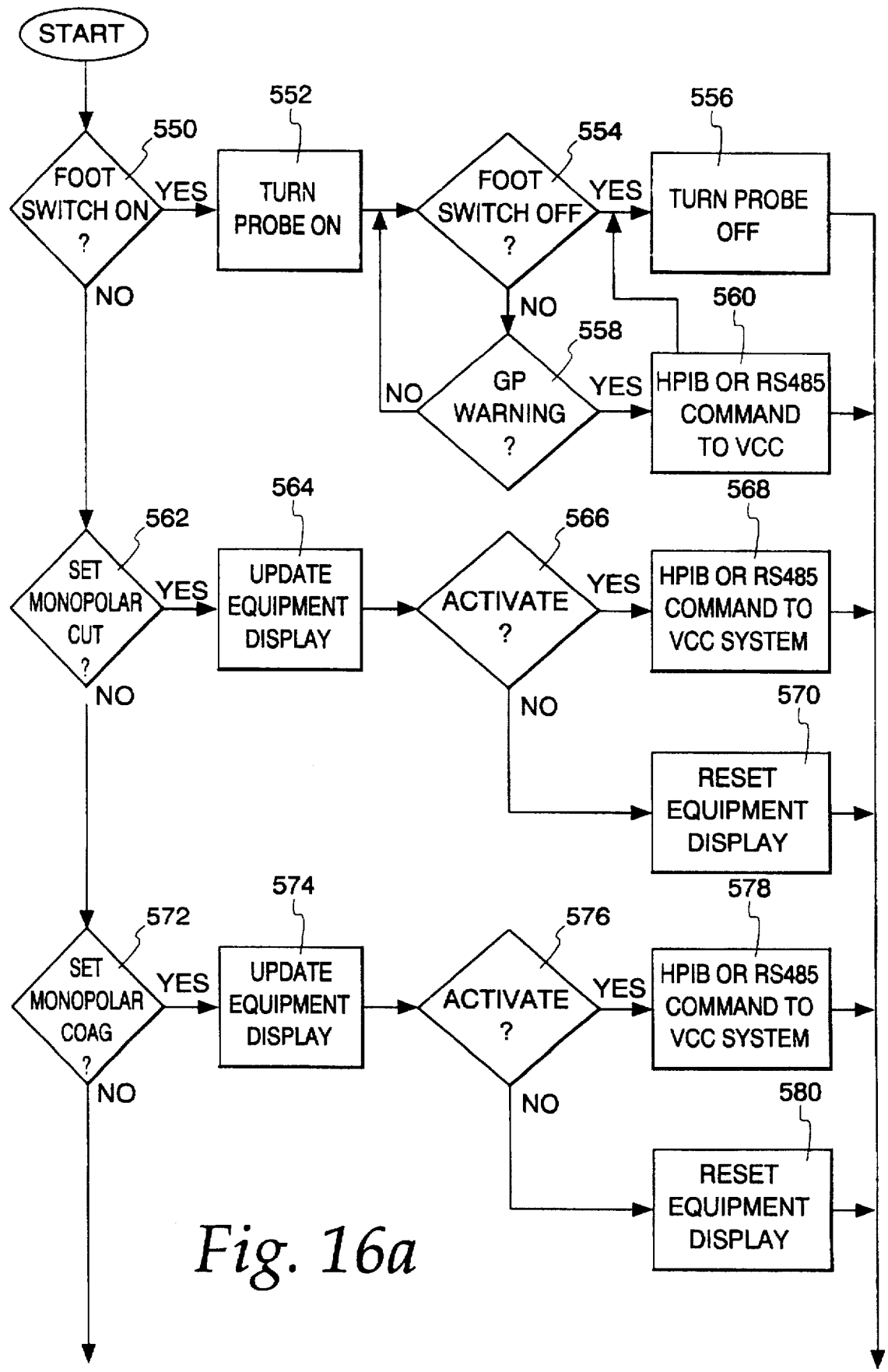
FIGS. 16A and 16B comprise a flow chart for an electrosurgical monopolar unit.
Figures 16A, 16B:
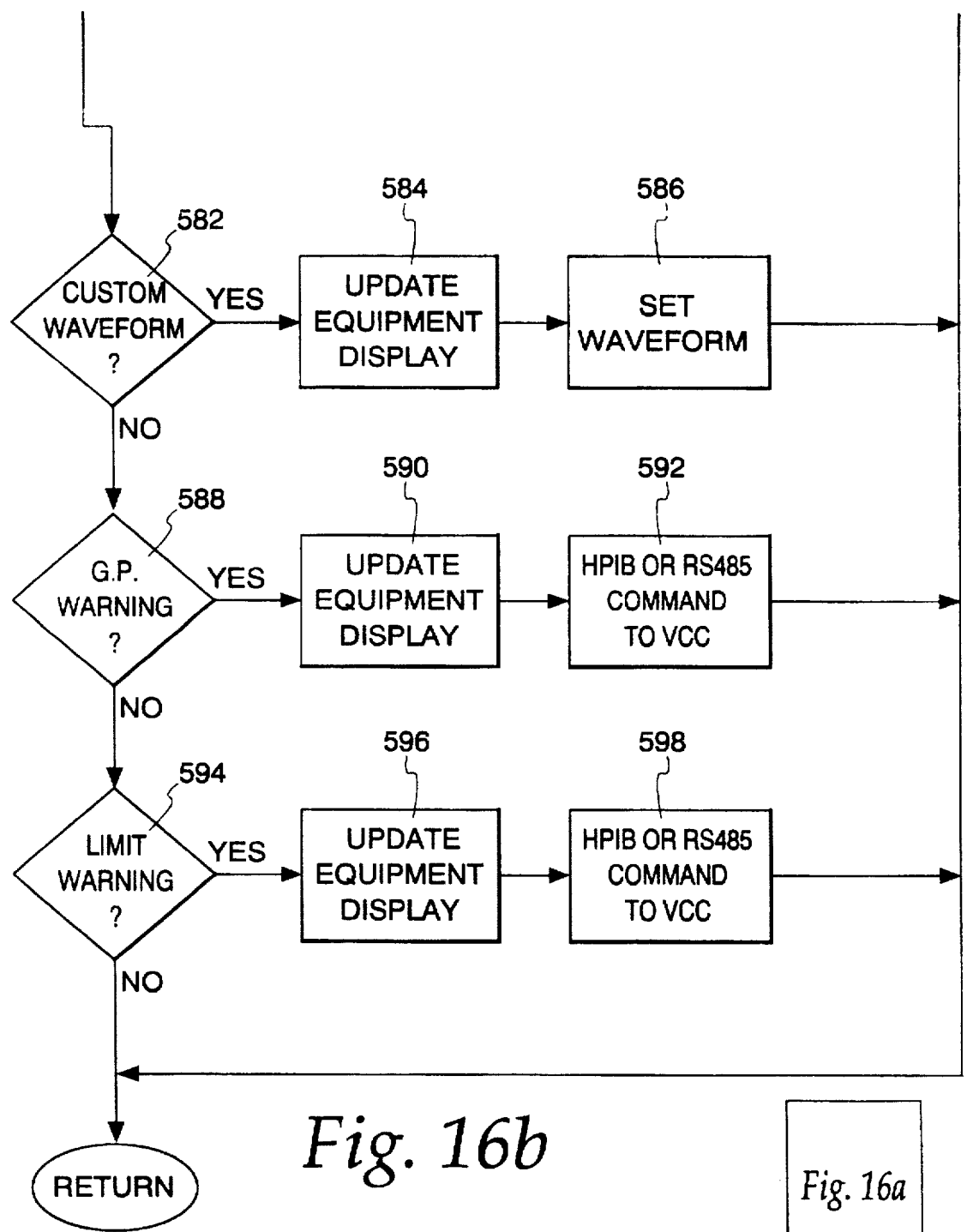

FIGS. 16A and 16B illustrate logic flow for the electrosurgical monopolar electrosurgical unit 44. Control begins at a decision block 550 which determines if the foot switch is on. If so, then the probe 54 is turned on at a block 552. A decision block 554 determines if the foot switch is off. If so, then the probe 54 is turned off at a block 556 and the routine ends as by returning to the start of the loop. If the switch is not off, as determined at the block 554, then a decision block 558 determines if there is a ground fault error. If not, then control loops back to the block 554. If there is a ground fault error, then a HPIB command indicating the error is sent to the SCC system 40 at a block 560 and control returns to the block 556 to turn the probe off.

If the foot switch is not on, as determined at the decision block 550, then a decision block 562 determines if monopolar cut has been set. If so, then the equipment display is updated at a block 564. A decision block 566 determines if the request has been activated by hitting an enter key. If so, then the HPIB command is sent to the SCC system 40 at a block 568. If not, within a preset time, then the equipment display is reset at a block 570 and the routine ends.

If the foot switch is not on, as determined at the decision block 560, then a decision block 572 determines if monopolar coag has been set. If so, then the equipment display is updated at a block 574. A decision block 576 determines if the request has been activated by hitting an enter key. If so, then the HPIB command is sent to the SCC system 40 at a block 578. If not, within a preset time, then the equipment display is reset at a block 580 and the routine ends.

If monopolar coag was not set at the decision block 572, then a decision block 582 determines if a custom waveform has been selected. If so, then the equipment display is updated at a block 584 and the waveform is set at a block 586. The routine then ends.

If a custom waveform was not set, then a decision block 588 determines if there is a ground fault error. If so, then the equipment display is updated at a block 590 and an HPIB command is set to the SCC system 40 at a block 592 and the routine ends. If there is no ground fault error, then a decision block 594 determines if there is a limit error. If so, then the equipment display is updated at a block 596 and the HPIB command is sent to the SCC system 40 at a block 598 and the routine ends.

Figure 17:
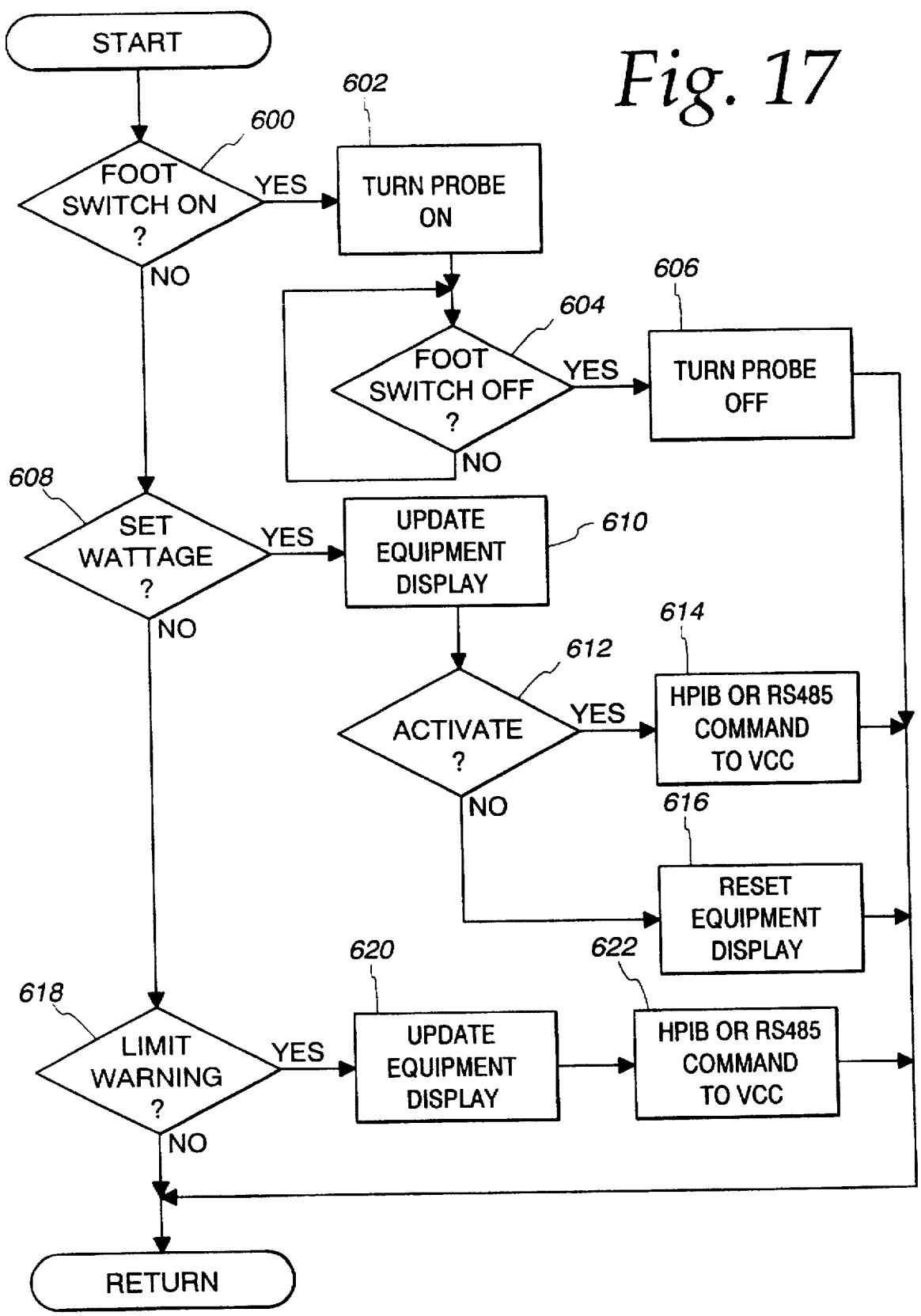
FIG. 17 is a flow chart of an electrosurgical bipolar unit.

FIG. 17 illustrates a flow chart for the bipolar electrosurgical unit 46 of FIG. 1. This control begins at a decision block 600, which determines if a foot switch is on. If so, then a probe 60 is turned on at a block 602. A decision block 604 loops upon itself until the foot switch is turned off, at which time the probe is turned off at a block 606 and the routine ends.

If the foot switch is not on, as determined at the block 600, then a decision block 608 determines if a wattage change has been set. If so, then the equipment display is updated at a block 610. A decision block 612 waits a preselect time until the wattage setting is activated. If so, then an HPIB command is sent to the SCC system 40 at a block 614. If not, then the display is reset at a block 616 and the routine ends.

If the wattage change is not made at the decision block 608, then a decision block 618 determines if there is a limit error. If so, then the equipment display is updated at a block 620 and HPIB command is sent to the SCC system 40 at a block 622 and the routine ends.

Figure 2A:
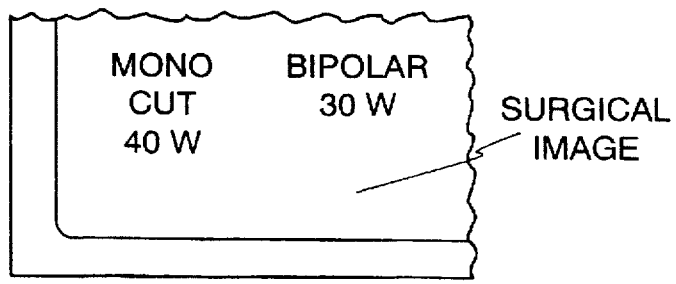
FIG. 2A is a detail view of a portion of a display on the monitor of FIG. 2.

As discussed above, the HUD display on the monitor 68 comprise a video image from the camera 74, as shown on the image in FIG. 2. Also on the HUD display can be additional information relating to the pieces of surgical equipment being used. In the illustration of FIG. 2, four separate fields, A, B, C and D, are illustrated for showing display information. As can be appreciated, the display information can be shown anywhere on the display screen and can occupy separate portions of the screen, as in FIG. 2, or can overwrite the display image from the camera 74, see FIG. 2A.

The format of the HUD information added to the camera video image for display is developed from the symbols in the block 700 of FIG. 18, showing the various symbols available. Boxes are used to encapsulate and separate like areas while triangles, circles and hexagons are used to emulate the switches as they exist on the surgeon's sterile panel 124. The lightning bolt symbol 702 indicates Electrosurgical unit or laser activation. The alphanumeric characters and computer generated graphics can be laid into a number of visual formats to achieve desired effects. The various formats either subdue or highlight the data on the HUD display to achieve readability without creating an overbearing intrusion or annoyance on the surgeon video image. The display example 704 shows a continuous display for a bipolar electrosurgical unit indicating that it is set to cut with a 30 watt setting, as illustrated by the numeric value of 30 watts. The bar graph representation shows the amperage through the bipolar probe and therefore the surgeon can measure the degree of electrodesiccation within the tissues as the current is continually applied to the probe.

For the HUD display, symbols and alphanumeric characters are combined to make up three basic groups of displays, continuous, expanded and warnings.

Examples of continuous displays are shown in FIGS. 19A–19D. Continuous displays are smaller boxes for abbreviated information the surgeon selects from the control panel and is located at the bottom of the screen, at respective locations A, B, C and D of FIG. 2. FIG. 19A illustrates a monopolar wattage display. FIG. 19B illustrates a bipolar wattage display. FIG. 19C illustrates $CO_2$ laser wattage. Finally, FIG. 19D illustrates intra-abdominal pressure. Other programmable displays may be added or interchanged with the illustrated displays, as necessary or desired.

Continuous displays are toggled on and off by the surgeon with the clear/cont push button 706 on the panel 124, see FIG. 4. If surgeon feels the continuous displays are intrusive, then the surgeon may switch one or more of the displays off with one touch of the button for a full screen video. However, even when off, the system continues to monitor the component devices and update memory appropriately. If critical value is reached or violated, then the appropriate continuous display box will appear on the screen along with a warning indicator.

The expanded HUD mode simply provides the surgeon with a video image of the entirety of the particular surgical device's control head. These displays mimic the functional areas as seen on the surgeon's sterile panel, thus replicating the equipment control head. The expanded display is intended to ease the task of information gathering and problem solving and allows a surgical team to work directly off the video screen. These display areas are selected by pressing the long rectangular block containing the name of the functional area on the surgeon's panel 124, such as the rectangular block showing the word "insufflation". Only one expanded display will show up at a time, since they are larger and take up valuable screen space. If one expanded display is on and another selected, the first disappears and is overwritten with the new display.

Finally, displays are generated to warn the surgeon about error conditions. If a predetermined upper or lower limit is reached on wattage settings, the appropriate continuous display box appears along with a warning box to let the surgeon know the limit violation. As in all warning displays, the problem must be fixed before the warning disappears. During monopolar operation, a ground fault error occurs if the ground plate disconnects from the electrosurgical equipment. During bipolar operation, a bar graph reflects current flow through the probe so the surgeon knows when desiccation is complete, the current decreases as moisture escapes from the tissue. In both monopolar and bipolar modes, when the surgeon activates the probe hand switch, the appropriate continuous display appears, if not already displayed, and a lightning bolt indicates an active probe.

Thus, in accordance with the invention, an endoscopic surgery command and control system comprises an independent computer-based electronic device that unifies the various pieces of equipment currently found in an endoscopic surgical suite into a surgeon-centered system. The system utilizes programmable software to simplify equipment management tasks that currently encumber the surgeon and operating room staff. It also enhances safety, and increases the utility of the individual pieces of equipment.

We claim:

1. In an endoscopic operating environment defining a surgeon's operating station at which a surgical procedure is performed with a plurality of self-contained independently and simultaneously operable pieces of surgical equipment, each including a surgical control head located at a non-sterile area remote from the surgeon's operating station and associated devices developing an output in response to commands manually entered directly at the surgical control head for driving an associated surgical instrument located at the surgeons operating station, a surgeon's command and control system comprising:

a surgeon's control panel operatively positioned at the surgeon's operating station, the surgeon's control panel including display means for displaying data relating to status of each of the plurality of self-contained pieces of surgical equipment and input means for receiving commands entered manually;

a plurality of communication interface circuits, one for each of said plurality of self-contained pieces of surgical equipment, each for transmitting data representing status of the associated surgical control head and for receiving remote commands for driving the associated self-contained surgical instrument; and a central controller operatively connected to each said communication interface circuit and said surgeon's control panel, said central controller transmitting to said plurality of self-contained pieces of surgical equipment commands entered manually on the surgeon's control panel and transmitting to said surgeon's control panel status of the surgical control heads for display on said display means to provide a surgeon direct command and control of the plurality of self-contained pieces of surgical equipment located in the non-sterile area remote from the surgeon's operating station, whereby each of the plurality of self-contained pieces of surgical equipment can be simultaneously operated with the operation thereof controlled and monitored from the surgeon's operating station.

2. The surgeon's command and control system of claim 1 further comprising an endoscopic camera electrically connected to said central controller for developing video image signal for a surgical procedure and a video monitor electrically connected to said central controller for displaying video images from the camera.

3. The surgeon's command and control system of claim 2 wherein said central controller includes a video frame store card operatively connected between said camera and said display monitor for storing frames of video data for display on said display monitor.

4. The surgeon's command and control system of claim 3 wherein said central controller includes means for transmitting to said frame store card status for the plurality of self-contained surgical devices for display on the video display monitor.

5. The surgeon's command and control system of claim 4 wherein said display monitor displays video images from said camera with select fields overwritten to display status information.

6. The surgeon's command and control system of claim 1 wherein said central controller comprises a programmed central processing unit operated in accordance with a program stored in associated memory devices.

7. The surgeon's command and control system of claim 6 wherein said memory devices store status and command data received by said central controller.

8. The surgeon's command and control system of claim 1 further comprising a microphone located at the surgeon's operating station and said central controller further comprises a speech recognition circuit for converting audio commands entered by a surgeon to digital signals to be transmitted to said plurality pieces of surgical equipment.

9. The surgeon's command and control system of claim 1 wherein said control panel comprises a control panel that is sterilized to avoid transfer of microorganisms from the control panel to a user.

10. A surgical control system, comprising:

a surgeon's operating station at which a surgical procedure is performed;

first and second self-contained and simultaneously operable pieces of surgical equipment each for performing a surgical procedure and including a surgical control head located at an area remote from the surgeon's operating station and associated devices developing a variable output for driving an associated surgical instrument located at the surgeons operating station, each self-contained piece of surgical equipment including means for producing a signal indicative of the output to each surgical instrument and means for receiving a variable control signal, the output varying in response to variations of the control signal;

first and second communication interface circuits for transmitting data representing status of the surgical control heads and for receiving remote commands for driving each of the self-contained surgical instruments;

a surgeon's control panel operatively positioned at the surgeon's operating station, the control panel including display means for displaying data relating to the output to each of the surgical instruments and input means for receiving commands entered manually;

a central controller operatively connected to said communication interface circuits and said surgeon's control panel, said central controller developing and transmitting to each said self-contained piece of surgical equipment the variable control signal from commands entered manually on the surgeon's control panel and transmitting to said surgeon's control panel data relating to the output of each of the surgical instruments for display on said display means to provide a surgeon direct command and control of the self-contained pieces of surgical equipment located in the non-sterile area remote from the surgeon's operating station, whereby each of the plurality of self-contained pieces of surgical equipment can be simultaneously operated with the operation thereof controlled and monitored from the surgeon's operating station.

11. The surgical control system of claim 10 further comprising an endoscopic camera electrically connected to said central controller for developing video image signal for a surgical procedure and a video monitor electrically connected to said central controller for displaying video images from the camera.

12. The surgical control system of claim 11 wherein said central controller includes a video frame store card operatively connected between said camera and said display monitor for storing frames of video data for display on said display monitor.

13. The surgical control system of claim 12 wherein said central controller includes means for transmitting to said frame store card status for the self-contained surgical devices for display on the video display monitor.

14. The surgical control system of claim 13 wherein said display monitor displays video images from said camera with select fields overwritten to display status information.

15. The surgical control system of claim 10 wherein said central controller comprises a programmed central processing unit operated in accordance with a program stored in associated memory devices.

16. The surgical control system of claim 15 wherein said memory devices store status and command data received by said central controller.

17. The surgical control system of claim 10 further comprising a microphone located at the surgeon's operating station and said central controller further comprises a speech recognition circuit for converting audio commands entered by a surgeon to digital signals to be transmitted to said pieces of surgical equipment.

18. The surgical control system of claim 10 wherein said control panel comprises a control panel that is sterilized to avoid transfer of microorganisms from the control panel to a user.

19. The surgical control system of claim 15 wherein said memory devices store preset equipment settings for use during a surgical procedure and said central controller transmits said settings to said self-contained pieces of surgical equipment during the surgical procedure.

20. The surgical control system of claim 15 wherein said memory devices store initial preset equipment settings for a surgical procedure and said central controller transmits said settings to each said self-contained piece of surgical equipment at the initiation of the surgical procedure.

21. The surgical control system of claim 10 wherein each said self-contained piece of surgical equipment includes a programmed central processing unit developing the variable output and wherein each said piece of surgical equipment is adapted to include an emulator circuit electrically and operatively disposed between the central processing unit and associated original equipment in each self-contained piece of surgical equipment, the emulator circuit including buffer circuitry to interface the central processing unit to the means for receiving the variable control signal.

22. The surgical control system of claim 21 wherein the emulator circuit is operatively associated with software algorithms to provide self diagnostics and to evaluate dynamic conditions and send appropriate status information to the central controller.

* * * * *